United States Patent
Narimatsu et al.

(10) Patent No.: US 6,719,704 B2
(45) Date of Patent: Apr. 13, 2004

(54) VASCULAR ENDOTHELIAL CELL FUNCTION EVALUATING APPARATUS

(75) Inventors: Kiyoyuki Narimatsu, Komaki (JP); Toshihiko Ogura, Komaki (JP); Akira Tampo, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 10/352,175

(22) Filed: Jan. 28, 2003

(65) Prior Publication Data

US 2003/0216652 A1 Nov. 20, 2003

(30) Foreign Application Priority Data

May 14, 2002 (JP) .................................. 2002-138099
Jun. 20, 2002 (JP) .................................. 2002-180369

(51) Int. Cl.[7] .............................................. A61B 5/02
(52) U.S. Cl. ............................. 600/500; 600/485
(58) Field of Search .......................... 600/300, 500, 600/483, 485, 492, 504, 490, 585, 561, 503, 502; 128/900; 514/12; 530/350; 482/8, 1, 9, 900; 73/727, 154, 156, DIG. 4

(56) References Cited

U.S. PATENT DOCUMENTS

| | | | | |
|---|---|---|---|---|
| 5,101,829 A | * | 4/1992 | Fujikawa et al. | 600/485 |
| 5,131,400 A | * | 7/1992 | Harada et al. | 600/500 |
| 5,179,956 A | * | 1/1993 | Harada et al. | 600/485 |
| 5,238,000 A | * | 8/1993 | Niwa | 600/502 |
| 5,848,970 A | * | 12/1998 | Voss et al. | 600/485 |
| 5,853,371 A | * | 12/1998 | Inukai et al. | 600/483 |
| 5,876,346 A | * | 3/1999 | Corso | 600/485 |
| 5,964,711 A | * | 10/1999 | Voss et al. | 600/485 |
| 6,132,337 A | * | 10/2000 | Krupka et al. | 482/8 |
| 6,210,340 B1 | * | 4/2001 | Amano et al. | 600/500 |
| 6,288,034 B1 | * | 9/2001 | Murgita | 514/12 |
| 6,312,387 B1 | * | 11/2001 | Nissila et al. | 600/500 |
| 6,491,647 B1 | * | 12/2002 | Bridger et al. | 600/585 |
| 6,554,774 B1 | * | 4/2003 | Miele | 600/485 |
| 6,575,915 B2 | * | 6/2003 | Nissila et al. | 600/500 |

* cited by examiner

Primary Examiner—Eric F. Winakur
Assistant Examiner—Nikita R Veniaminov
(74) Attorney, Agent, or Firm—Oliff & Berridge, PLC

(57) ABSTRACT

A vascular-endothelial-cell-function evaluating apparatus including a pressing device including a cuff that is adapted to be worn on a first portion of a living subject, and a cuff-pressure changing device that changes a pressure in the cuff so as to press the first portion of the subject in a pressing period, a pulse-wave detecting device that detects a pulse wave including a plurality of heartbeat-synchronous pulses, from the first portion of the subject, or a second portion of the subject located on a distal side of the first portion, and a pulse-wave-second-half-information obtaining device that obtains a plurality of sets of pulse-wave-second-half information that represent respective characteristics of respective second-half portions of respective heartbeat-synchronous pulses of the pulse wave that are detected by the pulse-wave detecting device at respective different times, the respective second-half portions of the respective heartbeat-synchronous pulses being respective portions of the respective pulses that are subsequent to respective peak points of the respective pulses, the pulse-wave-second-half-information obtaining device providing a time-wise change of the sets of pulse-wave-second-half information that is caused by the pressing of the pressing device.

12 Claims, 13 Drawing Sheets

VASCULAR ENDOTHELIAL CELL FUNCTION EVALUATING APPARATUS

BACKGROUND OF THE INVENTION

1. Field of the Invention

The present invention relates to a vascular-endothelial-cell-function evaluating apparatus that evaluates a function of vascular endothelial cells of a living subject.

2. Related Art Statement

Conventionally, the function of vascular endothelial cells of a living person is evaluated by imaging, using an ultrasound diagnostic device, a state in which blood vessels are dilated by administering a drug such as acetylcholine, or by pressing, using a cuff, a body portion of the person to stop a flow of blood in the body portion for several minutes and subsequently releasing the pressing of the cuff.

However, it is not recommended to administer any drugs in a living person. In addition, an ultrasound diagnostic device is expensive, and is not easy to use. Thus, the evaluation of vascular-endothelial-cell function is not practiced so widely.

SUMMARY OF THE INVENTION

It is therefore an object of the present invention to provide a vascular-endothelial-cell-function evaluating apparatus that can easily evaluate the function of vascular endothelial cells of a living subject.

The Inventors have carried out extensive studies and found that if a body portion of a living subject is pressed using a cuff, the diameter of blood vessels is changed by the pressing of the cuff, and that as the diameter of blood vessels is changed, a reflected-wave component of a pulse wave obtained from the cuff or a distal body portion of the subject located on a distal side of the cuff, is also changed. The Inventors have additionally found that the degree of change of the reflected-wave component of pulse wave that is caused by the change of diameter of blood vessels, depends on the condition of vascular endothelial cells of the subject. Here, the reflected-wave component of pulse wave mainly influences a waveform of a second half of a heartbeat-synchronous pulse of pulse wave, the second half being subsequent to a peak point of the pulse. Thus, the Inventors have finally found that the degree of change of pulse-wave-second-half information representing a characteristic of the second half of pulse wave, caused by the change of diameter of blood vessels, depends on the condition of vascular endothelial cells of the subject. The present invention has been developed based on these findings.

The above object has been achieved by the present invention. According to the present invention, there is provided a vascular-endothelial-cell-function evaluating apparatus comprising a pressing device including a cuff that is adapted to be worn on a first portion of a living subject, and a cuff-pressure changing device that changes a pressure in the cuff so as to press the first portion of the subject in a pressing period; a pulse-wave detecting device that detects a pulse wave including a plurality of heartbeat-synchronous pulses, from the first portion of the subject, or a second portion of the subject located on a distal side of the first portion; and a pulse-wave-second-half-information obtaining device that obtains a plurality of sets of pulse-wave-second-half information that represent respective characteristics of respective second-half portions of respective heartbeat-synchronous pulses of the pulse wave that are detected by the pulse-wave detecting device at respective different times, the respective second-half portions of the respective heartbeat-synchronous pulses being respective portions of the respective pulses that are subsequent to respective peak points of the respective pulses, the pulse-wave-second-half-information obtaining device providing a time-wise change of the sets of pulse-wave-second-half information that is caused by the pressing of the pressing device.

Here, the pressing period in which the cuff-pressure changing device changes the pressure in the cuff to press the first portion of the subject may be a prescribed time duration or a time duration defined by a prescribed operation such as a blood-pressure-measurement-related pressure changing operation, described later.

According to the present invention, the pulse-wave-second-half-information obtaining device obtains the plurality of sets of pulse-wave-second-half information, and provides the time-wise change of the sets of pulse-wave-second-half information that is caused by the pressing of the pressing device. It is possible to evaluate, based on the time-wise change of the sets of pulse-wave-second-half information, the function of vascular endothelial cells of the subject. Therefore, it is not needed to use an ultrasound diagnostic device and accordingly it is easy to evaluate the function of vascular endothelial cells.

According to a preferred feature of the present invention, the pressing device presses, with the cuff, the first portion of the subject so as to stop a flow of blood in the first portion, and subsequently decreases the pressure of the cuff down to a pressure not higher than a mean blood pressure of the first portion, and the pulse-wave-second-half-information obtaining device obtains the sets of pulse-wave-second-half information in a waveform-deformation period in which the pressure of the cuff has already been decreased to the pressure not higher than the mean blood pressure of the first portion and respective waveforms of the respective heartbeat-synchronous pulses of the pulse wave are deformed yet as a result of the pressing of the pressing device. According to this feature, in the waveform-deformation period in which the pressure of the cuff has already been decreased to the pressure not higher than the mean blood pressure of the first portion, after the cuff stops the flow of blood in the first portion of the subject, and the respective waveforms of the respective heartbeat-synchronous pulses of the pulse wave are deformed yet by the pressing of the pressing device, the pulse-wave-second-half-information obtaining device time-wise obtains the sets of pulse-wave-second-half information based on the respective waveforms of the respective heartbeat-synchronous pulses of the pulse wave detected by the pulse-wave detecting device. If the cuff stops the flow of blood in the first portion, the diameter of blood vessels decreases because no blood flows in the second portion located on the distal side of the cuff. However, thereafter, when the pressure of the cuff is decreased down to the pressure not higher than the mean blood pressure of the first portion, the diameter of blood vessels increases and temporarily exceeds an initial diameter in order to quickly supply blood to the second portion. Since the pulse-wave-second-half-information obtaining device time-wise obtains the sets of pulse-wave-second-half information after the pressure of the cuff has been decreased down to the pressure not higher than the mean blood pressure of the first portion, it can provide a great time-wise change of the sets of pulse-wave-second-half information. Thus, it is particularly easy to evaluate the function of vascular endothelial cells of the subject.

According to another feature of the present invention, the cuff-pressure changing device of the pressing device includes a blood-flow stopping device for increasing the pressure of the cuff up to a pressure higher than a systolic blood pressure of the first portion of the subject, so as to stop a flow of blood in the first portion; a first pulse-wave-detection-pressure keeping device for keeping, before the blood-flow stopping device increases the pressure of the cuff, the pressure of the cuff at a pulse-wave detection pressure not higher than a mean blood pressure of the first portion, for a time duration corresponding to at least one heartbeat of the subject; and a second pulse-wave-detection-pressure keeping device for keeping, after the blood-flow stopping device increases the pressure of the cuff, the pressure of the cuff at a pulse-wave detection pressure not higher than a mean blood pressure of the first portion, for a time duration corresponding to at least one heartbeat of the subject, the pulse-wave detecting device detects a cuff pulse wave that is transmitted from the first portion of the subject to the cuff, and the pulse-wave-second-half-information obtaining device obtains one of the sets of pulse-wave-second-half information from a cuff pulse wave detected by the pulse-wave detecting device in a state in which the pressure of the cuff is kept at the pulse-wave detection pressure by the first pulse-wave-detection-pressure keeping device, and obtains the other set of pulse-wave-second-half information from a cuff pulse wave detected by the pulse-wave detecting device in a state in which the pressure of the cuff is kept at the pulse-wave detection pressure by the second pulse-wave-detection-pressure keeping device. According to this feature, the pulse-wave-second-half-information obtaining device obtains the sets of pulse-wave-second-half information based on the respective pulse waves detected before the blood-flow stopping device stops the flow of blood in the first portion, and after the blood-flow stopping device completely stops the flow of blood in the first portion and subsequently sufficiently decreases the cuff pressure. Since the flow of blood in the first portion on which the cuff is worn is completely stopped once and subsequently the pressure of the cuff is sufficiently decreased, an amount of blood that flows in the second portion located on the distal side of the cuff temporarily exceeds an initial amount before the stopping. Therefore, it is possible to evaluate the function of vascular endothelial cells of the subject, based on a degree of change of the set of pulse-wave-second-half information obtained after the stopping, from the set of pulse-wave-second-half information obtained before the stopping.

According to another feature of the present invention, the cuff-pressure changing device of the pressing device further includes a pressure increasing device for increasing, before the first pulse-wave-detection-pressure keeping device keeps the pressure of the cuff at the pulse-wave detection pressure, the pressure of the cuff from a pressure lower than a diastolic blood pressure of the first portion of the subject, and the apparatus further comprises a pulse-wave-detection-pressure determining device for determining the pulse-wave detection pressure based on a fact that a deformation occurs to a waveform of a heartbeat-synchronous pulse of the cuff pulse wave continuously detected by the pulse-wave detecting device while the pressure of the cuff is increased by the pressure increasing device. According to this feature, the pulse-wave-detection-pressure determining device determines the pulse-wave detection pressure based on the pulse wave actually detected during the slow increasing of the cuff pressure. Thus, in each measuring operation, the most appropriate pulse-wave detection pressure is determined. Therefore, the respective pulse waves detected in the state in which the cuff pressure is kept at the pulse-wave detection pressure by the first pulse-wave-detection-pressure keeping device and in the state in which the cuff pressure is kept at the detection pressure by the second keeping device, have an accurate waveform, and accordingly the pulse-wave-second-half-information obtaining device obtains accurate sets of pulse-wave-second-half information based on the accurate pulse waves. Thus, it is possible to more accurately evaluate the function of vascular endothelial cells of the subject based on the accurate sets of pulse-wave-second-half information.

According to another feature of the present invention, the cuff-pressure changing device of the pressing device further includes a preliminary pressing device for increasing, before the first pulse-wave-detection-pressure keeping device keeps the pressure of the cuff at the pulse-wave detection pressure, the pressure of the cuff up to the pulse-wave detection pressure, by a predetermined number of times, so as to preliminarily press the first portion of the subject. According to this feature, the preliminary pressing device carries out the preliminary pressing of the first portion, and accordingly the cuff and the subcutaneous tissue of the first portion on which the cuff is worn are brought into close contact with each other. Therefore, a more accurate pulse wave can be detected and accordingly a more accurate set of pulse-wave-second-half information can be obtained based on the accurate pulse wave. Thus, it is possible to more accurately evaluate the function of vascular endothelial cells of the subject.

According to another feature of the present invention, the cuff-pressure changing device of the pressing device further includes a pressure increasing device for increasing, before the preliminary pressing device increases the pressure of the cuff, the pressure of the cuff from a pressure lower than a diastolic blood pressure of the first portion of the subject, and the apparatus further comprises a pulse-wave-detection-pressure determining device for determining the pulse-wave detection pressure based on a fact that a deformation occurs to a waveform of a heartbeat-synchronous pulse of the cuff pulse wave continuously detected by the pulse-wave detecting device while the pressure of the cuff is increased by the pressure increasing device.

According to another feature of the present invention, the blood-flow stopping device comprises a blood-pressure-measurement-related pressure changing device for increasing the pressure of the cuff up to the pressure higher than the systolic blood pressure of the first portion of the subject, and subsequently decreasing the pressure of the cuff, and the apparatus further comprises a blood-pressure determining device for determining a blood pressure of the subject based on a cuff pulse wave detected by the pulse-wave detecting device while the pressure of the cuff is decreased by the blood-pressure-measurement-related pressure changing device. According to this feature, the pulse-wave-second-half-information obtaining device time-wise obtains the sets of pulse-wave-second-half information of the subject, and additionally the blood-pressure determining device determines the blood pressure of the subject. Thus, it is possible to simultaneously evaluate the function of vascular endothelial cells, and obtain the blood pressure, of the subject.

According to another feature of the present invention, each of the sets of pulse-wave-second-half information comprises an augmentation index indicating a proportion of a reflected-wave component of the pulse wave to an incident-wave component thereof According to another feature of the present invention, each of the sets of pulse-wave-second-half information comprises a degree of sharpness of the pulse wave.

According to another feature of the present invention, each of the sets of pulse-wave-second-half information comprises a diastolic area of the pulse wave.

According to another feature of the present invention, the vascular-endothelial-cell-function evaluating apparatus further comprises a heart-rate-related-information obtaining device that obtains a plurality of sets of heart-rate-related information each of which is related to a heart rate of the subject, based on respective heartbeat-synchronous pulses of the pulse wave that are detected by the pulse-wave detecting device at respective different times, the heart-rate-related-information obtaining device providing a time-wise change of the sets of heart-rate-related information that is caused by the pressing of the pressing device. According to this feature, it is possible to judge, based on a change of the sets of heart-rate-related information that is caused by the pressing of the pressing device, whether the activity of the autonomic nerve of the subject is normal. Thus, it is possible to simultaneously evaluate the function of the vascular endothelial cells, and the activity of the autonomic nerve, of the subject.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
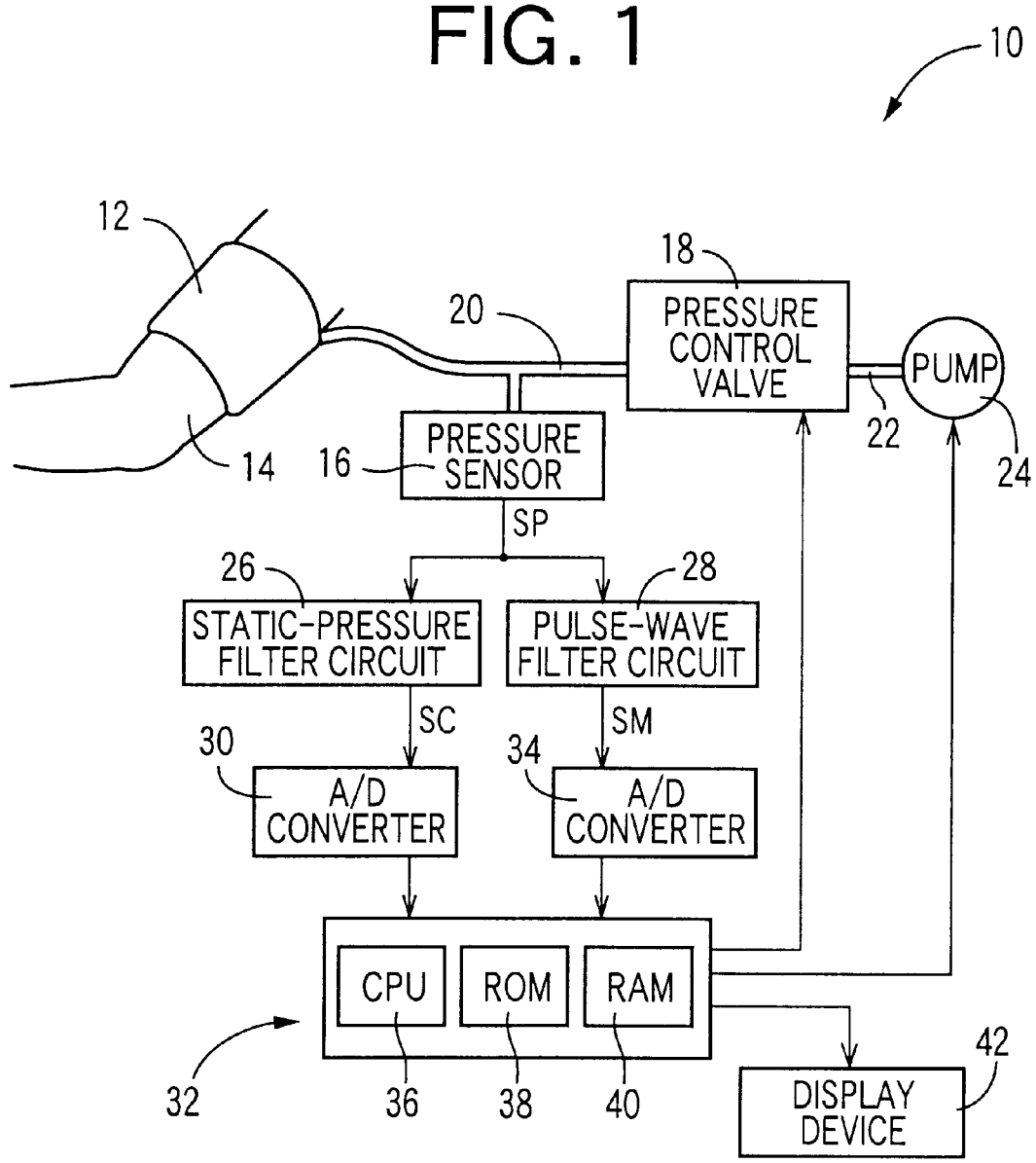
FIG. 1 is a diagrammatic view showing a circuitry of a vascular endothelial cell function evaluating apparatus to which the present invention is applied.

Hereinafter, there will be described an embodiment of the present invention in detail by reference to the drawings. FIG. 1 is a diagrammatic view showing a circuitry of a vascular endothelial cell function evaluating apparatus 10 to which the present invention is applied.

In FIG. 1, reference numeral 12 designates an inflatable cuff which includes a belt-like cloth bag and a rubber bag accommodated in the cloth bag and which is adapted to be wound around an upper arm 14 of a living subject as a body portion of the subject. The cuff 12 is connected via a piping 20 to a pressure sensor 16 and a pressure control valve 18. The pressure control valve 18 is connected via a piping 22 to an air pump 24. The pressure control valve 18 adjusts a pressure of a pressurized air supplied from the air pump 24, and supplies the pressure-adjusted air to the cuff 12, or discharges the pressurized air from the cuff 12, so as to control an air pressure in the cuff 12.

The pressure sensor 16 detects the air pressure in the cuff 12, and supplies a pressure signal, SP, representing the detected air pressure, to a static-pressure filter circuit 26 and a pulse-wave filter circuit (i.e., a pulse-wave filter device) 28. The static-pressure filter circuit 26 includes a low-pass filter that extracts, from the pressure signal SP, a cuff-pressure signal, SC, representing a static component of the detected air pressure, i.e., a pressing pressure of the cuff 12 (hereinafter, referred to as the cuff pressure, PC). The filter circuit 26 supplies the cuff-pressure signal SC to an electronic control device 32 via an A/D (analog-to-digital) converter 30. The pulse-wave filter circuit 28 includes a band-pass filter that permits passing of signals having frequencies of from 1 to 30 Hz and thereby extracts, from the pressure signal SP, a cuff-pulse-wave signal, SM, representing a cuff pulse wave as an oscillatory component of the detected air pressure. The filter circuit 28 supplies the cuff-pulse-wave signal SM to the control device 32 via an A/D converter 34. The cuff pulse wave represented by the cuff-pulse-wave signal SM is a pressure oscillation transmitted from a brachial artery of the subject to the cuff 12. In the present embodiment, the cuff 12, the pressure sensor 16, and the pulse-wave filter circuit 28 cooperate with each other to provide a pulse-wave detecting device.

The control device 32 is provided by a so-called microcomputer including a CPU (central processing unit) 36, a ROM (read only memory) 38, a RAM (random access memory) 40, and an I/O (input-and-output) port, not shown. The CPU 36 processes signals according to the control programs pre-stored in the ROM 38 by utilizing the temporary-storage function of the RAM 40, and supplies drive signals via the I/O port to the air pump 24 and the pressure control valve 18 so as to control the cuff pressure PC. Moreover, the CPU 36 has various functions shown in detail in FIG. 2 for time-wise determining respective augmentation index values AI and respective heart rate values HR of the subject, and controls what is displayed by a display device 42.

Figure 2:
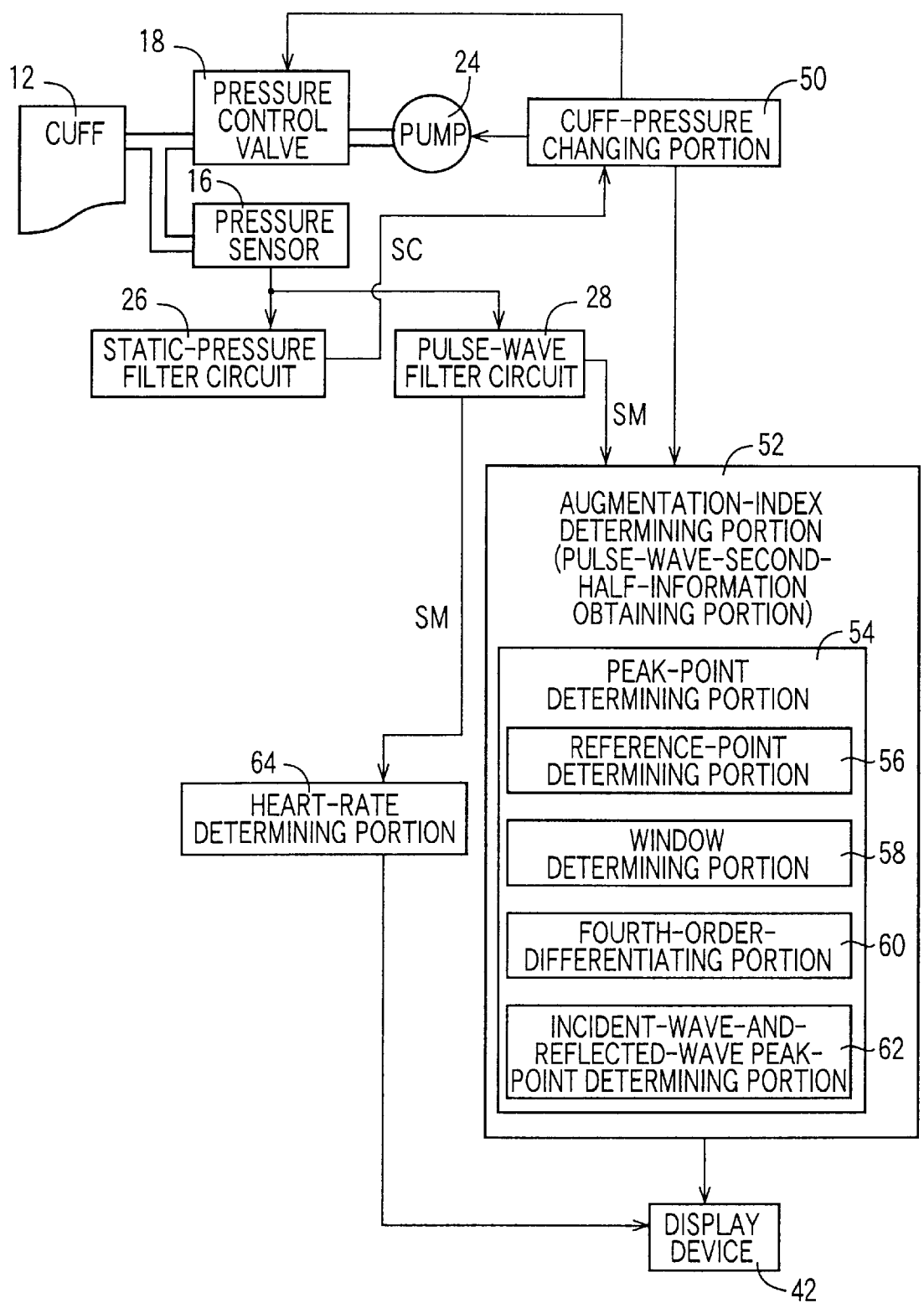
FIG. 2 is a block diagram for explaining essential control functions of a CPU (central processing unit) of the vascular endothelial cell function evaluating apparatus shown in FIG. 1.

FIG. 2 is a block diagram for explaining essential control functions of the control device 36 of the vascular endothelial cell function evaluating apparatus 10.

A cuff-pressure changing portion or means 50 operates, based on the cuff-pressure signal SC supplied from the static-pressure filter circuit 26, the pressure control valve 18 and the air pump 24, such that first the cuff pressure PC is kept at a blood-flow stopping pressure PC1 for a pre-determined blood-flow stopping period T1 and then the cuff pressure PC is kept at a pulse-wave detection pressure PC2 for a pre-determined measurement period T2. Thus, in the present vascular endothelial cell function evaluating apparatus 10, the cuff 12, the cuff-pressure changing portion 50, the static-pressure filter circuit 26 supplying the cuff-pressure signal SC to the cuff-pressure changing portion 50, and the pressure control valve 18 and the air pump 24 that are controlled by the cuff-pressure changing portion 50 cooperate with each other to provide a pressing device.

The blood-flow stopping period T1 is so pre-determined as to fall within a range from a very short time shorter than one minute, such as several seconds or several tens of seconds, to several minutes. The blood-flow stopping pressure PC1 is a cuff pressure PC that can stop flow of blood in the body portion on which the cuff 12 is worn, and is so pre-determined as to be higher than a systolic blood pressure $BP_{SYS}$ of the body portion on which the cuff 12 is worn.

The pulse-wave detection pressure PC2 is a cuff pressure PC that is used for detecting a cuff pulse wave to be used for determining an augmentation index, and is so pre-determined as to be lower than a mean blood pressure $BP_{MEAN}$, more preferably, a diastolic blood pressure $BP_{DIA}$, of the subject, and as to be not lower than a sufficiently high pressure, e.g., from 50 mmHg to 60 mmHg, that assures that a cuff pulse wave having a sufficiently great magnitude is detected. If the above-indicated pulse-wave detection pressure PC2 is higher than the diastolic blood pressure $BP_{DIA}$ of the subject, the cuff pulse wave extracted by the pulse-wave filter circuit 28 is deformed because the artery is pressed. In particular, if the pulse-wave detection pressure is higher than the mean blood pressure $BP_{MEAN}$ of the subject, the artery is so largely pressed and accordingly the cuff pulse wave is so largely deformed that an accurate augmentation index AI cannot be determined.

The measurement period T2 is a time period in which an augmentation-index determining portion or means 52, described later, time-wise determines augmentation index values AI, and is so pre-determined as to end before the waveform of cuff pulse wave, deformed by keeping the cuff pressure PC at the blood-flow stopping pressure PC1, returns to its initial state. Here, providing that a time period in which first the waveform of cuff pulse wave is deformed by starting the pressing of the cuff 12, then the pressing of the cuff 12 is ended, and finally the blood flow returns to its initial state and accordingly the waveform of cuff pulse wave returns to its initial state, is called a waveform deformation period, the measurement period T2 ends before the waveform deformation period ends.

The augmentation-index determining portion 52 iteratively determines respective augmentation index values AI, based on respective heartbeat-synchronous pulses of the cuff pulse wave extracted by the pulse-wave filter circuit 28 in the measurement period T2 started immediately after the cuff pressure PC is changed to the pulse-wave detection pressure PC2 by the cuff-pressure changing portion 50, and operates the display device 42 to display the thus determined augmentation index values AI. The augmentation-index determining portion 52 includes a peak-point determining portion or means 54 that determines a peak point P of an incident-wave component contained in the cuff-pulse-wave signal SM, a time $t_P$ of occurrence of the peak point P, a peak point R of a reflected-wave component of the signal SM, and a time $t_R$ of occurrence of the peak point R, and determines, according to a relationship represented by the following Expression 1, an augmentation index AI based on a pulse pressure (i.e., the greatest amplitude) PP of the cuff-pulse-wave signal SM and a difference ΔP (=b−a) obtained by subtracting a magnitude, a, of the cuff-pulse-wave signal SM at the time $t_P$ of occurrence of peak point P of the incident-wave component from a magnitude, b, of the cuff-pulse-wave signal SM at the time $t_R$ of occurrence of peak point R of the reflected-wave component:

$$AI=(\Delta P/PP)\times 100(\%) \quad \text{(Expression 1)}$$

Figure 3:
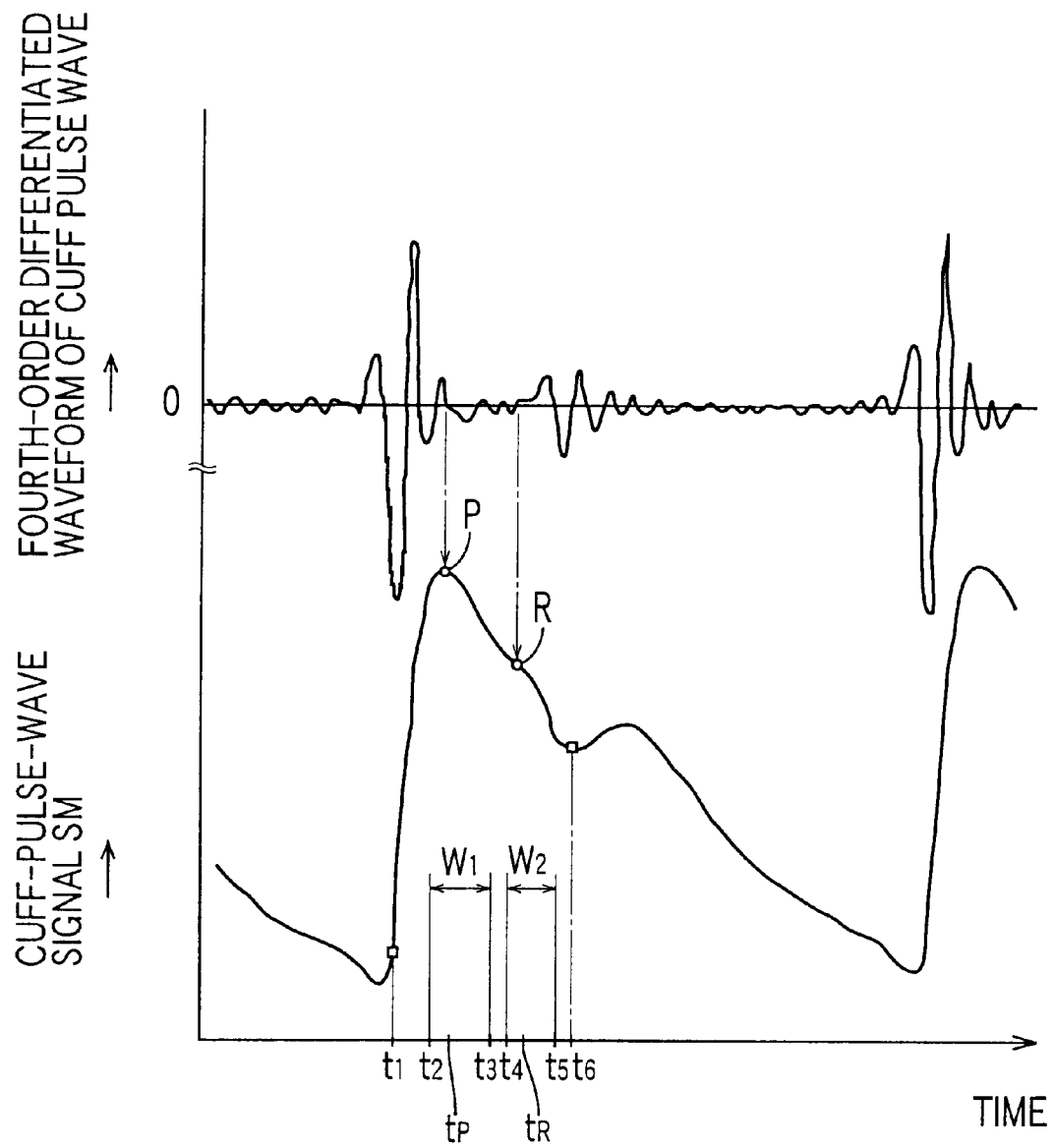
FIG. 3 is a time chart showing a relationship among a cuff pulse wave, a fourth-order-differentiated waveform, a rising-point window $W_1$, a notch-point window $W_2$, an incident-wave peak point P, and a reflected-wave peak point R.
Figure 4:
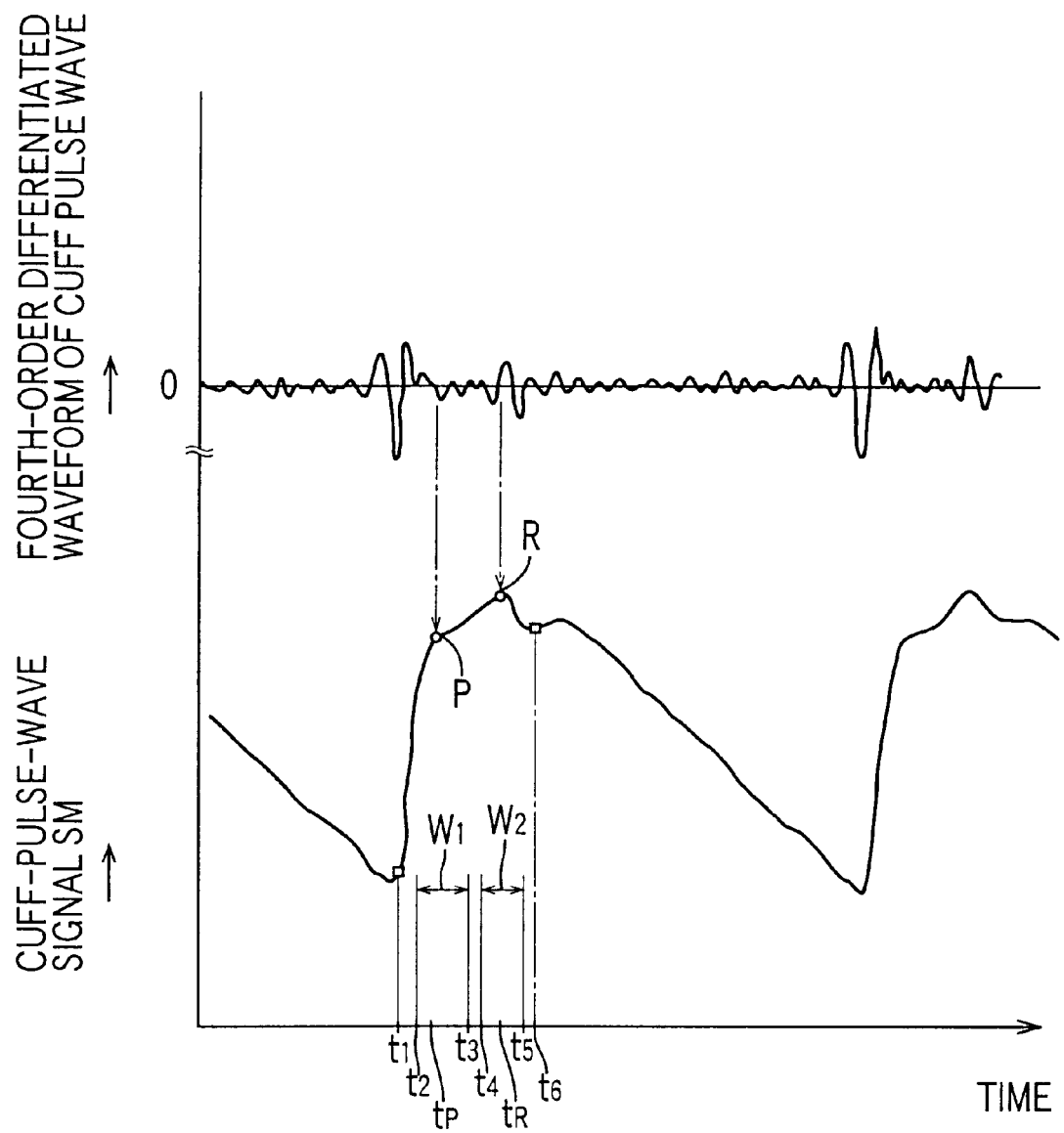
FIG. 4 is a time chart showing a relationship among a cuff pulse wave having a different waveform than that of the cuff pulse wave shown in FIG. 3, a fourth-order-differentiated waveform, a rising-point window $W_1$, a notch-point window $W_2$, an incident-wave peak point P, and a reflected-wave peak point R.

The peak-point determining portion 54 subjects the cuff-pulse-wave signal SM to fourth-order differentiation, and determines, based on the thus obtained fourth-order-differentiated waveform of the signal SM, more specifically, zero-crossing points of the differentiated waveform, a peak point P of an incident-wave component of the signal SM, a time $t_P$ of occurrence of the peak point P, a peak point R of a reflected-wave component of the signal SM, and a time $t_R$ of occurrence of the peak point R. FIGS. 3 and 4 show two cuff-pulse-wave signals SM having different waveforms, and their respective fourth-order-differentiated waveforms, respectively, and each of the FIGS. 3 and 4 shows the corresponding one signal SM and its differentiated waveform along a common time axis, and a peak point P of an incident-wave component of the signal SM, a time $t_P$ of occurrence of the peak point P, a peak point R of a reflected-wave component of the signal SM, and a time $t_R$ of occurrence of the peak point R. Since, as shown in FIGS. 3 and 4, a peak point of a heartbeat-synchronous pulse of the cuff pulse wave coincides with a peak point P of an incident-wave component of the pulse or a peak point R of a reflected-wave component of the pulse, an augmentation index AI determined based on a difference ΔP obtained by subtracting a magnitude, a, of the peak point P from a magnitude, b, of the peak point R, relates to a magnitude of the peak point of the cuff pulse wave. Thus, the augmentation index AI is a sort of pulse-wave-second-half information, and the augmentation-index determining portion 52 functions as a sort of pulse-wave-second-half-information obtaining device.

The peak-point determining portion 54 includes a reference-point determining portion or means 56 for determining, based on the waveform of the cuff-pulse-wave signal SM, reference points on the cuff pulse wave, i.e., a rising point $t_1$ and a notch point $t_6$; a window determining portion or means 58 for determining a rising-point window (i.e., a time gate) $W_1$ that starts and ends at a time $t_2$ and a time $t_3$, respectively, that are subsequent by respective prescribed times to the rising point $t_1$, and additionally determining a notch-point window (a time gate) $W_2$ that starts and ends at a time $t_4$ and a time $t_5$, respectively, that are prior by respective prescribed times to the notch point $t_6$; a fourth-order differentiating portion or means 60 for fourth-order differentiating, i.e., four times differentiating the cuff-pulse-wave signal SM obtained in the state in which the cuff pressure PC is kept at the pulse-wave detection pressure PC2; and an incident-and-reflected-wave peak-point determining portion or means 62 for determining, based on two zero-crossing points of the thus obtained fourth-order differentiated waveform that fall within the rising-point window $W_1$ and the notch-point window $W_2$, respectively, a peak point P of an incident-wave component of the cuff-pulse-wave signal SM, a time $t_P$ of occurrence of the peak point P, a peak point R of a reflected-wave component of the cuff-pulse-wave signal SM, and a time $t_R$ of occurrence of the peak point R. The reference-point determining portion 56 determines, as a rising point $t_1$, a point that is subsequent to a local minimum point of a heartbeat-synchronous pulse of the cuff pulse wave and has a magnitude equal to a predetermined proportion, e.g., one tenth, of an amplitude between the minimum point and a maximum point of the heartbeat-synchronous pulse, and additionally determines, as a notch point $t_6$, the first local minimum point, or the first inflection point, subsequent to the maximum point. The incident-and-reflected-wave peak-point determining portion 62 determines, as a time $t_P$ of occurrence of peak point of an incident-wave component, a zero-crossing point that has a pre-determined position as counted from the start point of the rising-point window $W_1$, e.g., the first zero-crossing point falling in the rising-point window $W_1$, and crosses zero in a direction from a positive area to a negative area; and additionally determines, as a time $t_R$ of occurrence of peak point of a reflected-wave component, a zero-crossing point that has a pre-determined position as counted from the start point of the notch-point window $W_2$, e.g., the first zero-crossing point falling in the notch-point window $W_2$, and crosses zero in a direction from the negative area to the positive area. The respective times from the rising point $t_1$ to the start and end points of the rising-point window $W_1$ and the respective times from the notch point $t_6$ to the start and end points of the notch-point window $W_2$, employed by the window determining portion 58, are experimentally determined in advance so that the times $t_P$, $t_R$ fall in the widows $W_1$, $W_2$, respectively.

A medical person such as a doctor can judge, based on a time-wise change of the augmentation index values AI iteratively determined in the measurement period T2 and displayed by the display device 42, whether the function of vascular endothelial cells of the subject is normal. More specifically described, if the function of vascular endothelial cells is normal, the augmentation index values AI determined based on the pulse wave detected from the pressed body portion whose blood flow is once stopped, or a downstream body portion located downstream of the pressed body portion, gradually decrease as the diameter of artery gradually increases after the blood flow is once stopped and subsequently is resumed. However, if the function of vascular endothelial cells is abnormal, that is, if the arteries have hardened and accordingly the function of the arteries has lowered, the augmentation index values AI determined for the abnormal arteries do not decrease at all, or do not decrease by the same amount as that by which the index values AI determined for the normal arteries decrease.

A heart-rate determining portion or means 64 functioning as a heart-rate-related-information obtaining device iteratively determines respective heart rate values HR of the subject, based on a time interval between respective prescribed periodic points (e.g., respective rising points or respective peak points) of each pair of successive heartbeat-synchronous pulses of the cuff pulse wave extracted by the pulse-wave filter circuit 28 in the measurement period T2 in which the cuff pressure PC is kept at the pulse-wave detection pressure PC2 by the cuff-pressure changing portion 50, and operates the display device 42 to display the thus determined heart rate values HR. The medical person can know, from the heart rate values HR iteratively determined by the heart-rate determining portion 64 in the measurement period T2 and displayed by the display device 42, a time-wise change of the heart rate values HR that occurs when the blood flow is once stopped and subsequently is resumed, and evaluate, based on a degree of the change, the activity of autonomic nerve of the subject.

Figure 5:
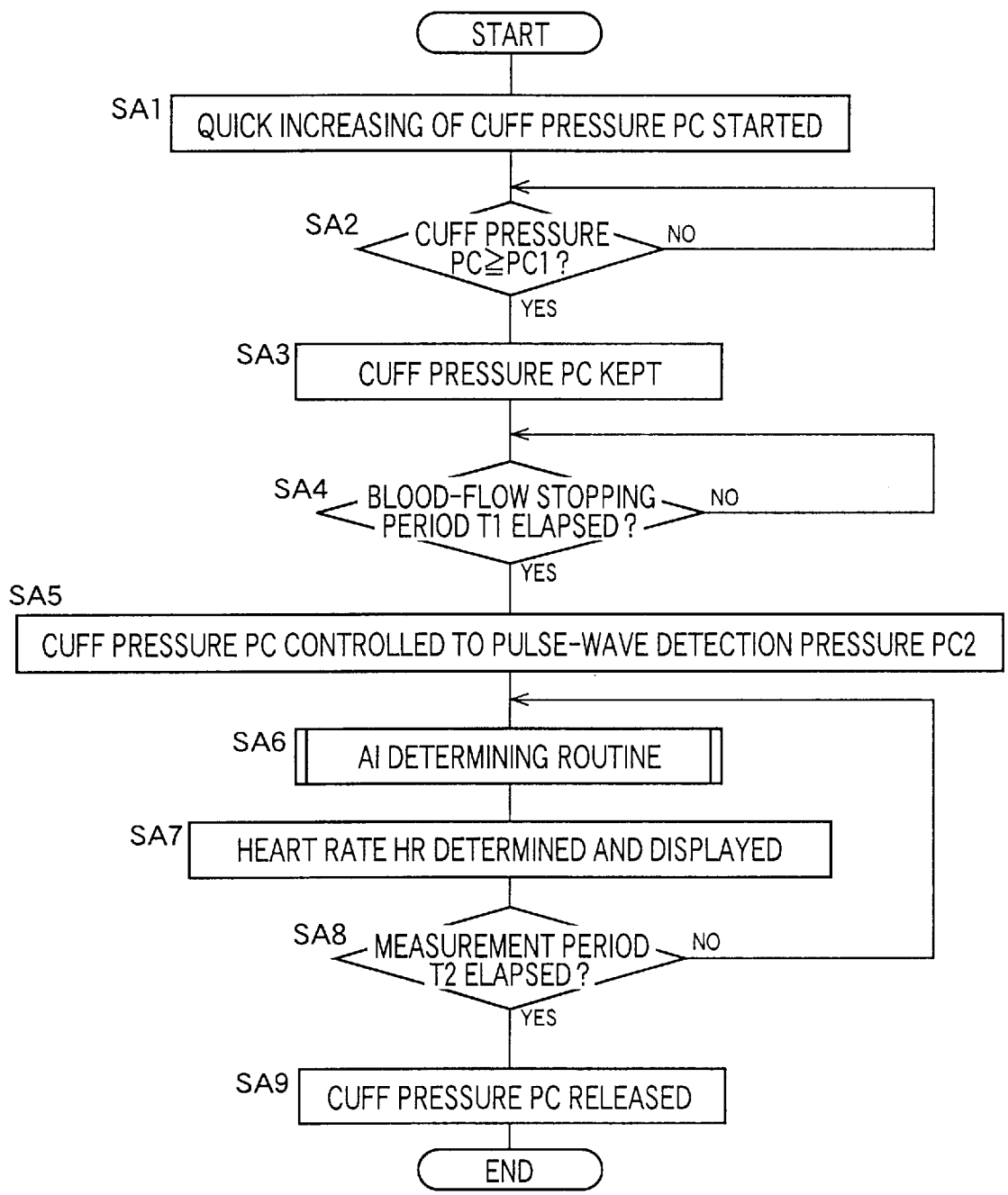
FIG. 5 is a flow chart for explaining the essential control functions of the CPU, shown in FIG. 2.

FIG. 5 is a flow chart representing the control functions of the CPU 36, shown in the block diagram of FIG. 2.

In FIG. 5, when a measurement starting operation, not shown, is carried out, the control of the CPU starts with Step SA1 (hereinafter, the term "Step" is omitted). At SA1, the CPU operates the air pump 24 and the pressure control valve 18 so as to start quick increasing of the cuff pressure PC, at a time, ta, shown in FIG. 6. Then, the control goes to SA2 to judge whether the cuff pressure Pc has reached the blood-flow stopping pressure PC1, e.g., 180 mmHg. SA2 is repeated until a positive judgment is made, while the cuff pressure PC is quickly increased.

Figure 6:
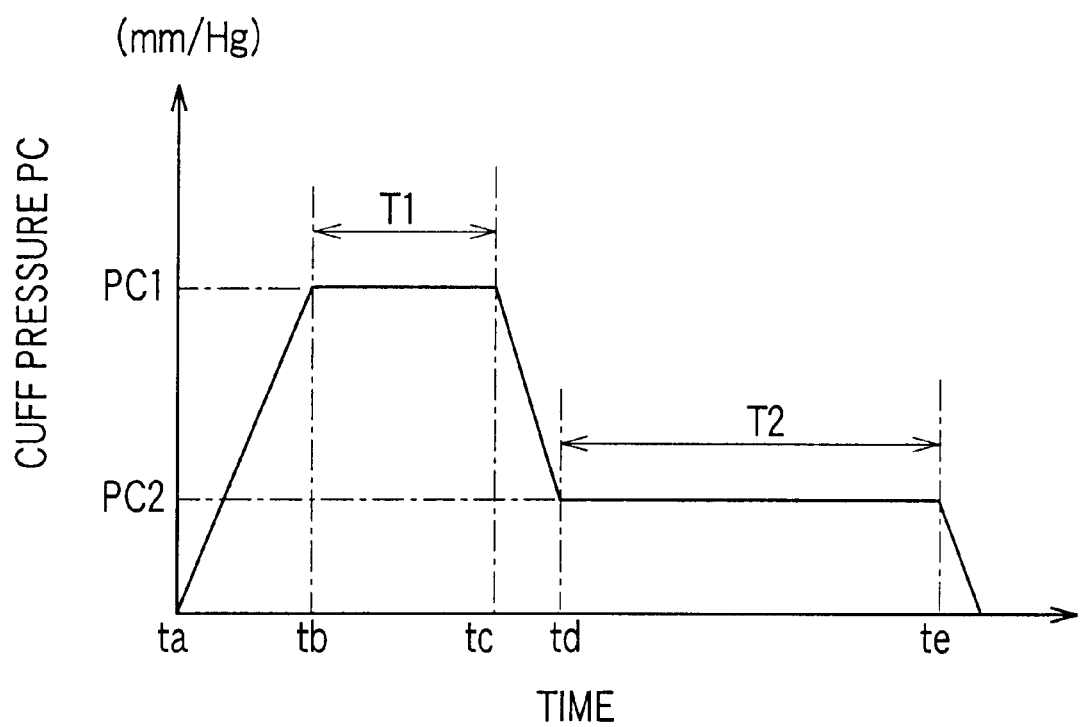
FIG. 6 is a time chart showing a time-wise change of a cuff pressure PC when the flow chart of FIG. 5 is carried out.

Meanwhile, at a time, tb, shown in FIG. 6, a positive judgment is made at SA2, the control goes to SA3 to stop the air pump 24 and operate the pressure control valve 18 so as to keep the cuff pressure Pc to the pressure PC1. Then, at SA4, the CPU judges whether a time duration that has elapsed since the cuff pressure PC was kept at SA3 has exceeded the blood-flow stopping period T1, e.g., 30 seconds. SA4 is repeated till a positive judgment is made, while the cuff pressure PC is kept to the pressure PC1.

Meanwhile, at a time, tc, shown in FIG. 6, a positive judgment is made at SA4, the control goes to SA5 to operate again the pressure control valve 18 so as to keep the cuff pressure PC to the pulse-wave detection pressure PC2, e.g., 50 mmHg, at a time, td, shown in FIG. 6. Then, the control goes to SA6 corresponding to the augmentation-index determining portion 52, i.e., an augmentation-index determining routine shown in FIG. 7.

Figure 7:
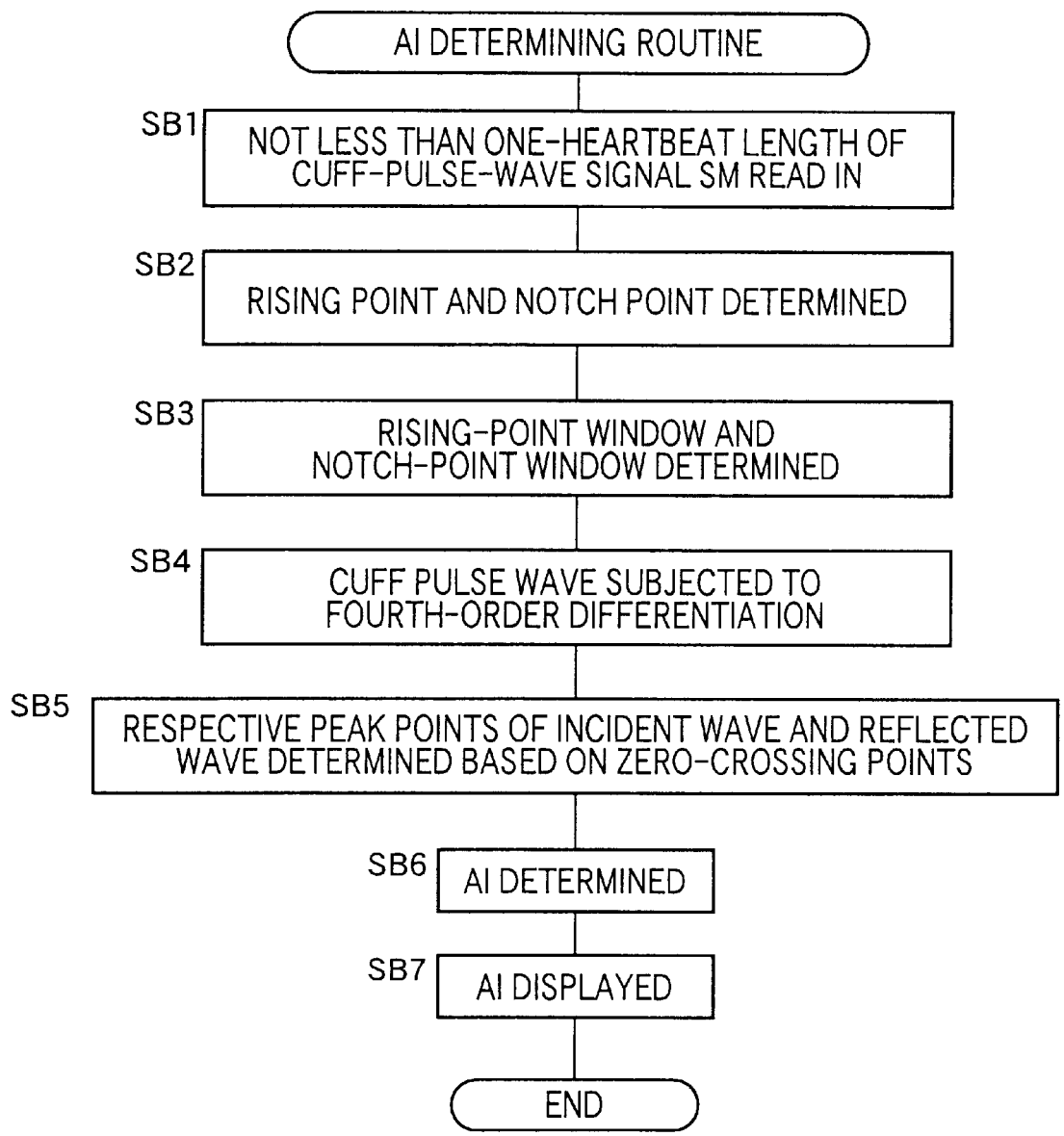
FIG. 7 is a flow chart for explaining an AI determining routine employed in the flow chart of FIG. 5.

First, at SB1 of FIG. 7, the CPU reads in a more than one heartbeat length of the cuff pulse wave represented by the cuff-pulse-wave signal SM, i.e., reads in a length of the signal SM that lasts from a prescribed periodic point (e.g., a rising point or a peak point) of a heartbeat-synchronous pulse of the cuff pulse wave to a corresponding periodic point (e.g., a rising point or a peak point) of the next heartbeat-synchronous pulse of the cuff pulse wave.

Subsequently, the control of the CPU proceeds with SB2 corresponding to the reference-point determining portion 56. At SB1, the CPU determines, based on the waveform of the cuff pulse wave represented by the cuff-pulse-wave signal SM obtained from the cuff 12 the pressure of which is kept at the pulse-wave detection pressure PC2, reference points on the cuff pulse wave, i.e., a rising point $t_1$ and a notch point $t_6$. For example, the CPU determines, as the rising point $t_1$, a point that is subsequent to a minimum point of a heartbeat-synchronous pulse of the cuff pulse wave and has a magnitude equal to a predetermined proportion, e.g., one tenth, of an amplitude between the minimum point and a maximum point of the heartbeat-synchronous pulse, and additionally determines, as the notch point $t_6$, the first local minimum point, or the first inflection point, subsequent to the maximum point.

Subsequently, the control goes to SB3 corresponding to the window determining portion 58. At SB3, the CPU determines a rising-point window (i.e., a time gate) $W_1$ that starts and ends at a time $t_2$ and a time $t_3$, respectively, that are subsequent by respective prescribed times to the rising point $t_1$, and additionally determining a notch-point window (a time gate) $W_2$ that starts and ends at a time $t_4$ and a time $t_5$, respectively, that are prior by respective prescribed times to the notch point $t_6$.

Subsequently, the control goes to SB4 corresponding to the fourth-order differentiating portion 60. At SB4, the CPU subjects, to fourth-order differentiation, the cuff-pulse-wave signal SM obtained from the cuff 12 the pressure of which is kept at the pulse-wave detection pressure PC2. Then, the control goes to SB5 corresponding to the incident-and-reflected-wave peak-point determining portion 62. At SB5, the CPU determines, based on two zero-crossing points of the thus obtained fourth-order differentiated waveform that fall within the rising-point window $W_1$ and the notch-point window $W_2$, respectively, a peak point P of an incident-wave component of the cuff-pulse-wave signal SM, a time $t_P$ of occurrence of the peak point P, a peak point R of a reflected-wave component of the signal SM, and a time $t_R$ of occurrence of the peak point R.

Figure 8:
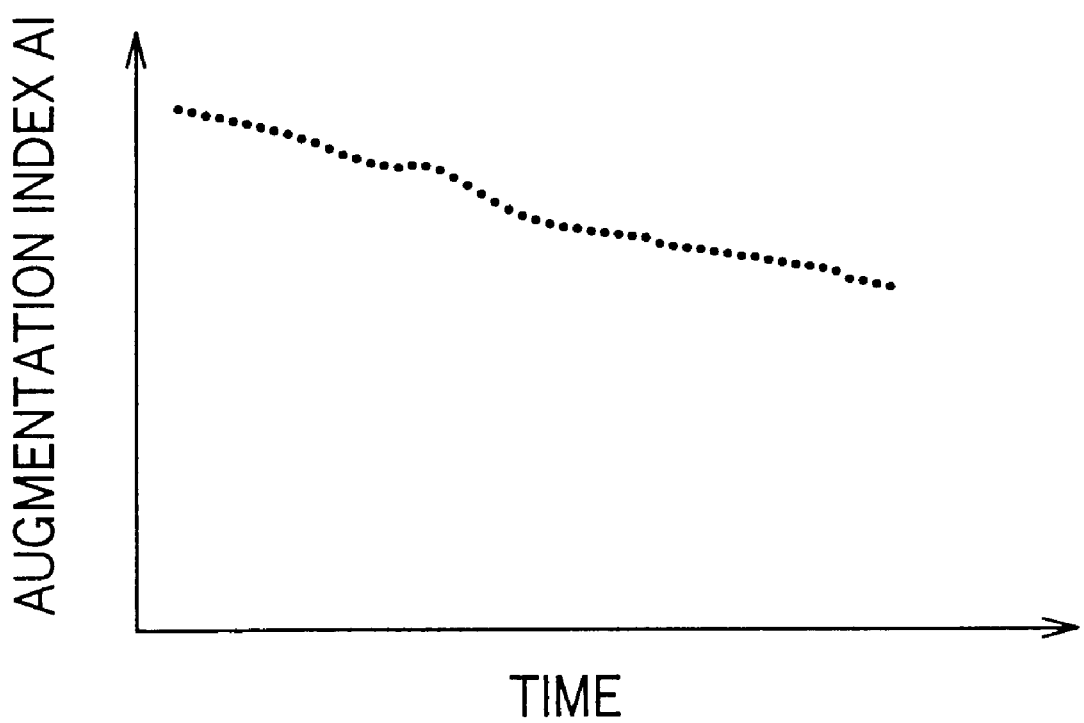
FIG. 8 is a time chart showing a time-wise change of respective augmentation index values AI displayed by a display device when Step SA6 of FIG. 5 is carried out.

Subsequently, at SB6, the CPU first determines a pulse pressure (i.e., the greatest amplitude) PP of the cuff-pulse-wave signal SM obtained from the cuff 12 the pressure of which is kept at the pulse-wave detection pressure PC2, and then determines a difference ΔP (=b−a) by subtracting a magnitude, a, of the cuff-pulse-wave signal SM at the time $t_P$ of occurrence of peak point of the incident-wave component of the signal SM from a magnitude, b, of the signal SM at the time $t_R$ of occurrence of peak point of the reflected-wave component of the signal SM. Moreover, the CPU determines, according to the relationship represented by the above-indicated Expression 1, an augmentation index AI based on the pulse pressure PP and the difference ΔP. Then, at SB7, the CPU operates the display device 42 to display, as shown in FIG. 8, the augmentation index AI determined at SB6, at a prescribed area in an image screen of the display device 42.

Back to FIG. 5, the control goes to SA7 corresponding to the heart-rate determining portion 64. At SA7, the CPU determines, as a pulse period, RR, (seconds), a time interval between the respective prescribed periodic points of the two successive heartbeat-synchronous pulses of the cuff pulse wave, read in at SB1 of FIG. 7, subsequently replaces the thus determined pulse period RR for the following Expression 2, so as to determine a heart rate, HR, (times/min), of the subject, and operates the display device 42 to display the thus determined heart rate HR:

$$HR=60/RR \qquad \text{(Expression 2)}$$

Then, at SA8, the CPU judges whether a time duration that has elapsed since the cuff pressure PC was kept to the pulse-wave detection pressure P2 at SA5 has exceeded the measurement period T2, e.g., 1 minute. SA8 is repeated till a positive judgment is made, while respective augmentation index values AI and respective heart rate values HR are successively determined and displayed.

Meanwhile, at a time, te, shown in FIG. 6, a positive judgment is made at SA8, the control goes to SA9 to operate the pressure control valve 18 so as to release the cuff pressure Pc down to atmospheric pressure.

It emerges from the foregoing description of the present embodiment that the augmentation-index determining portion 52 (SA6) time-wise determines the respective augmentation index values AI of the subject based on the cuff pulse wave detected by the pulse-wave filter circuit 28 in the measurement period T2 in which the cuff pressure PC is kept at the pulse-wave detection pressure PC2 after the flow of blood in the upper arm 14 is stopped with the cuff 12. Thus, the medical person can evaluate, based on the time-wise change of the respective augmentation index values AI, the function of vascular endothelial cells of the subject. Since it is not needed to employ a ultrasound diagnostic device, it is easy to evaluate the function of vascular endothelial cells.

Also, in the present embodiment, the heart-rate determining portion 64 (SA7) time-wise determines the respective heart rate values HR of the subject based on the cuff pulse wave detected by the pulse-wave filter circuit 28 in the measurement period T2 in which the cuff pressure PC is kept at the pulse-wave detection pressure PC2 after the flow of blood in the upper arm 14 is stopped with the cuff 12. Thus, the medical person can evaluate, based on the time-wise change of the respective heart rate values HR, the activity of the autonomic nerve of the subject. Thus, the medical person can simultaneously evaluate both the function of the vascular endothelial cells and the activity of the autonomic nerve.

Next, a second embodiment of the present invention will be described by reference to the drawings. The same reference numerals as used in the first vascular endothelial cell function evaluating apparatus 10 shown in FIGS. 1 to 8 are used to designate the corresponding elements of the second embodiment, and the description of those elements is omitted.

Figure 9:
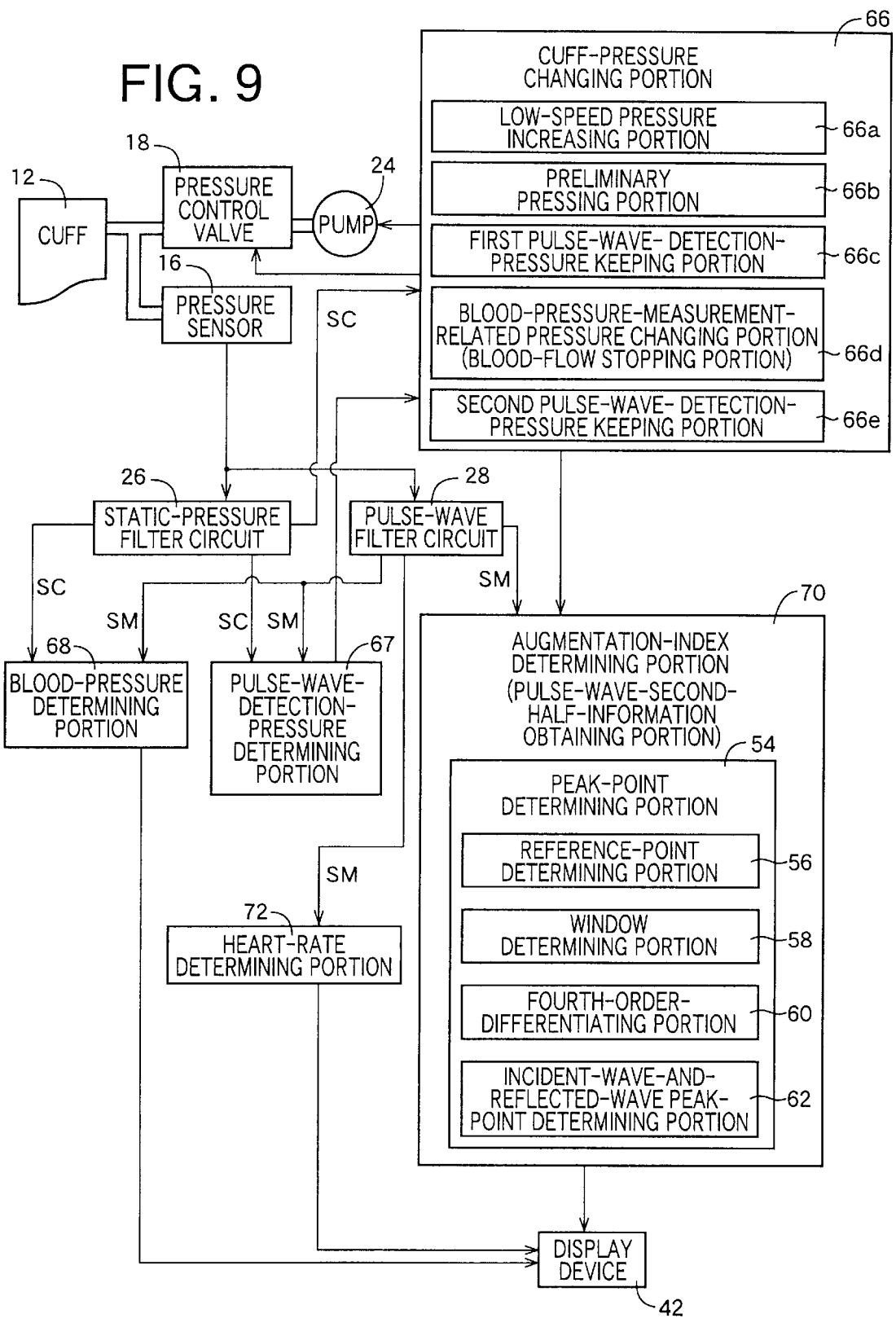
FIG. 9 is a block diagram for explaining essential control functions of a CPU of another vascular endothelial cell function evaluating apparatus different from the apparatus shown in FIG. 1.

FIG. 9 is a block diagram for explaining essential control functions of a CPU 36 of a vascular endothelial cell function evaluating apparatus as the second embodiment of the present invention. The second embodiment differs from the first embodiment only with respect to some control functions of the CPU 36.

A cuff-pressure changing portion or means 66 includes a low-speed pressure increasing portion or means 66a; a preliminary pressing portion or means 66b that is operated after the low-speed pressure increasing portion 66a; a first pulse-wave-detection-pressure keeping portion or means 66c that is operated after the preliminary pressing portion 66b; a blood-pressure-measurement-related pressure changing portion or means 66d that is operated after the first pulse-wave-detection-pressure keeping portion 66c; and a second pulse-wave-detection-pressure keeping portion or means 66e that is operated after the blood-pressure-measurement-related pressure changing portion 66d.

The low-speed pressure increasing portion 66a increases, at a low speed, a cuff pressure PC from atmospheric pressure as a pressure sufficiently lower than a diastolic blood pressure of a body portion 14 around which a cuff 12 is worn, and continues the low-speed pressure increasing till a pulse-wave-detection-pressure determining portion or means 67, described later, determines a pulse-wave detection pressure PC2. Here, the low speed is, e.g., from 2 to 5 mmHg/sec. The increasing of the cuff pressure PC may be continuous (i.e., linear) or discontinuous (i.e., stepwise).

The preliminary pressing portion 66b carries out a prescribed number (e.g., from one to three) of preliminary pressing operations each of which includes increasing the cuff pressure PC up to the pulse-wave detection pressure PC2 determined by the pulse-wave-detection-pressure determining portion 67, described later and, immediately after the cuff pressure PC has reached the pulse-wave detection pressure PC2, or after the cuff pressure PC is kept at the pressure PC2 for a prescribed time duration (e.g., several seconds), decreasing the cuff pressure PC down to the atmospheric pressure. Each of the first and second pulse-wave-detection-pressure keeping portions 66c, 66e keeps, for a time duration corresponding to not less than one heartbeat of the subject, the cuff pressure PC to the pulse-wave detection pressure PC2 determined by the pulse-wave-detection-pressure determining portion 67, described later.

The blood-pressure-measurement-related pressure changing portion 66d, also functioning as a blood-flow stopping device, carries out a prescribed number (e.g., one) of blood-pressure measuring operations. More specifically described, in each blood-pressure measuring operation, the blood-pressure-measurement-related pressure changing portion 66d quickly increases the cuff pressure PC up to a target pressure value, PCm, (e.g., 180 mmHg) that would be higher than a systolic blood pressure $BP_{SYS}$ of the upper arm 14, and subsequently decreases, at a low speed of from 2 to 3 mmHg/sec, the cuff pressure PC till a blood-pressure determining portion or means 68, described later, finishes determining blood-pressure values BP of the subject.

The pulse-wave-detection-pressure determining portion or means 67 determines the pulse-wave detection pressure PC2 based on a fact that respective waveforms of respective lower portions of a plurality of heartbeat-synchronous pulses of the cuff pulse wave that are successively detected by the pulse-wave filter circuit 28 are deformed little by little as the cuff pressure PC is slowly increased by the low-speed pressure increasing portion 66a. In the state in which the upper arm 14 is pressed by the cuff 12, the oscillation of blood pressure in the body portion 14 being pressed by the cuff 12 does not occur in a pressure range lower than the current cuff pressure PC. Therefore, if the cuff pressure PC increases and eventually exceeds a diastolic blood pressure $BP_{DIA}$ of the subject, a waveform of a lower portion of a heartbeat-synchronous pulse of the cuff pulse wave is deformed. Since it is preferred that a pulse-wave detection pressure PC2 is somewhat lower than the diastolic blood pressure $BP_{DIA}$ of the subject, the determining portion 67 determines the pulse-wave detection pressure PC2 by subtracting a prescribed small value (e.g., 20 mmHg) from a current cuff pressure PC at the time when deformation first occurs to the respective waveforms of the respective lower portions of the heartbeat-synchronous pulses of the cuff pulse wave successively detected during the slow increasing of cuff pressure PC. Here, whether deformation first occurs to the respective waveforms of the respective lower portions of the heartbeat-synchronous pulses of the cuff pulse wave is judged as follows: Each of the respective waveforms of the successive heartbeat-synchronous pulses of the cuff pulse wave is normalized, subsequently a difference of an area defined by the normalized waveform of the each pulse from an area defined by the normalized waveform of a pulse preceding the each pulse is calculated, and then it is judged whether a rate or amount of change of the differences calculated from the respective waveforms of the successive heartbeat-synchronous pulses has exceeded a prescribed reference value. If the rate or amount of change has exceeded the reference value, it can be judged that deformation first occurs to the cuff pulse wave.

The blood-pressure determining portion or means 68 determines, based on change of respective amplitudes of a plurality of heartbeat-synchronous pulses of the cuff pulse wave represented by the cuff-pulse-wave signal SM continuously obtained during the slow decreasing of the cuff pressure Pc under the control of the blood-pressure-measurement-related pressure changing portion 66d, a systolic blood pressure $BP_{SYS}$, a mean blood pressure $BP_{MEAN}$, and a diastolic blood pressure $BP_{DIA}$ of the subject, according to well-known oscillometric method. In addition, the determining portion 68 operates the display device 42 to display the thus determined systolic blood pressure $BP_{SYS}$, etc.

An augmentation-index determining portion or means 70 differs from the augmentation-index determining portion 52 employed in the first embodiment, only with respect to time of determination of augmentation index AI. The augmentation-index determining portion 70 determines, like the augmentation-index determining portion 52 employed in the first embodiment, an augmentation index value AI based on each of the respective cuff pulse waves supplied from the pulse-wave filter circuit 28 when the cuff pressure PC is kept at the pulse-wave detection pressure PC2 by the first pulse-wave-detection-pressure keeping portion 66c and when the cuff pressure PC is kept at the pulse-wave detection pressure PC2 by the second pulse-wave-detection-pressure keeping portion 66e, i.e., when the cuff pressure PC is kept at the pulse-wave detection pressure PC2 immediately before and after the blood-pressure-measurement-related pressure changing operation carried out by the blood-pressure-measurement-related pressure changing portion 66d. In addition, the determining portion 70 operates the display device 42 to display the thus determined augmentation index values AI. In the case where the determining portion 70 determines the respective augmentation index values AI before and after the blood-pressure measuring operation, since the upper arm 14 is pressed by the cuff 12 during the blood-pressure measuring operation, a medical person can observe a time-wise change of the augmentation index values AI that is caused by the pressing of the cuff 12.

A heart-rate-determining portion or means 72, functioning as a heart-rate-related-information obtaining device, also differs from the heart-rate determining portion 64 employed in the first embodiment, with respect to time of determination of heart rate HR. The heart-rate determining portion 72 determines a heart rate HR based on each of the cuff pulse waves used by the augmentation-index determining portion 70 to determine the augmentation index values AI, and operates the display device 42 to display the thus determined heart rate values HR. That is, the determining portion 72 also determines a heart rate HR based on each of the respective cuff pulse waves supplied from the pulse-wave filter circuit 28 when the cuff pressure PC is kept at the cuff-pressure detection pressure PC2 before and after the blood-pressure-measurement-related pressure changing operation carried out by the blood-pressure-measurement-related pressure changing portion 66d.

Figure 10:
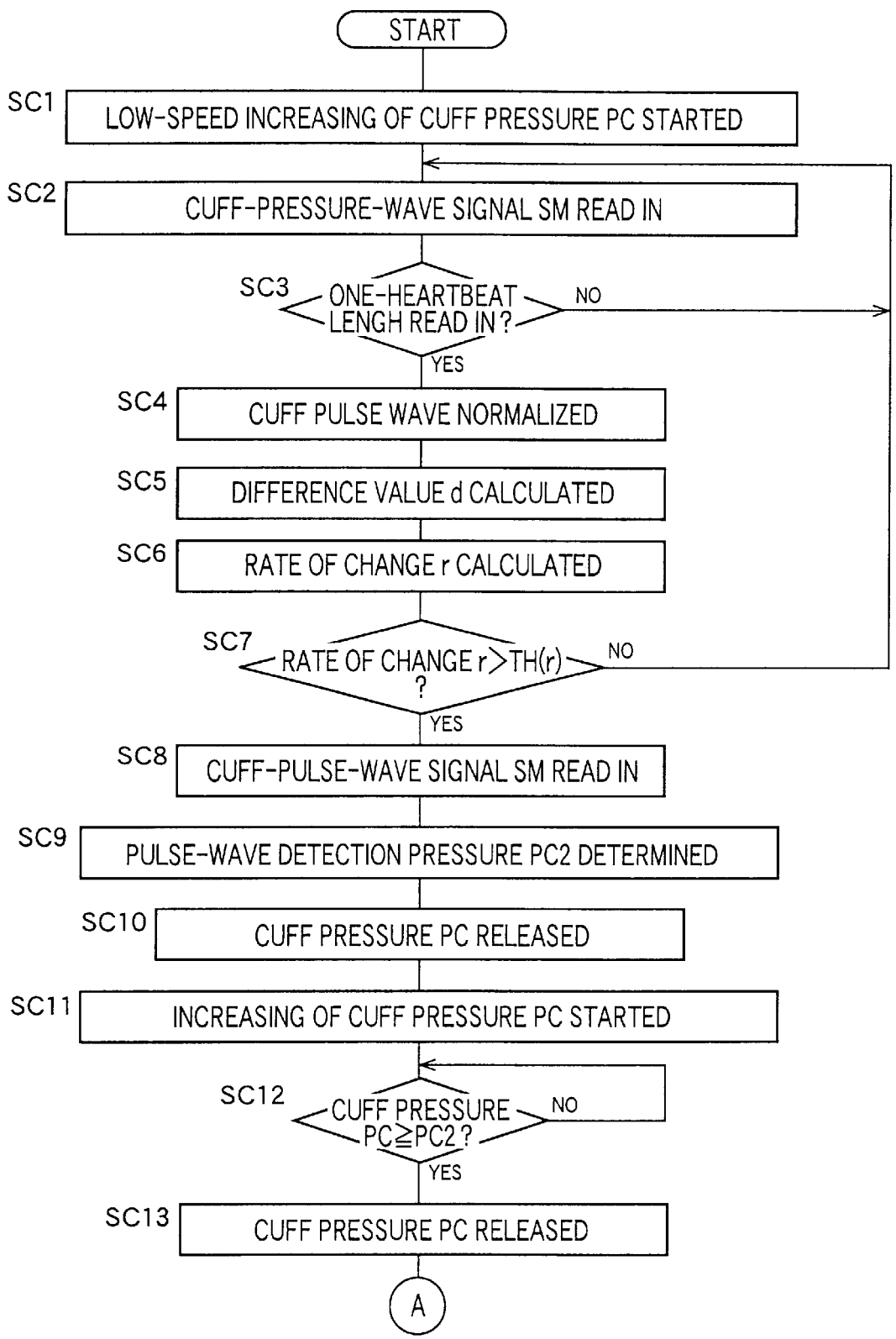
FIG. 10 is a flow chart for explaining the essential control functions of the CPU, shown in FIG. 9.
Figure 11:
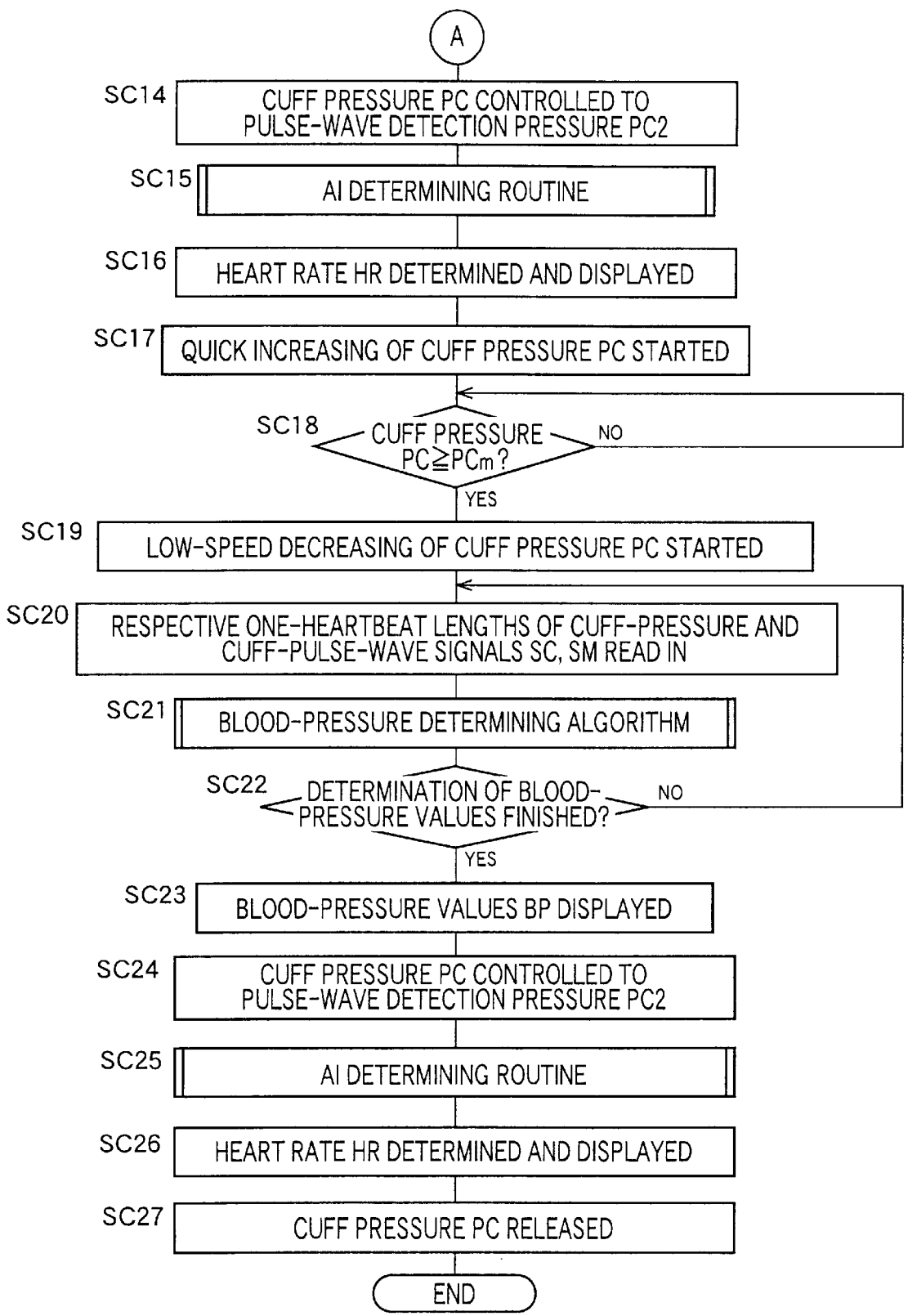
FIG. 11 is another flow chart for explaining the essential control functions of the CPU, shown in FIG. 9.

FIGS. 10 and 11 are flow charts representing the control functions of the CPU 36, shown in the block diagram of FIG. 9.

Figure 12:
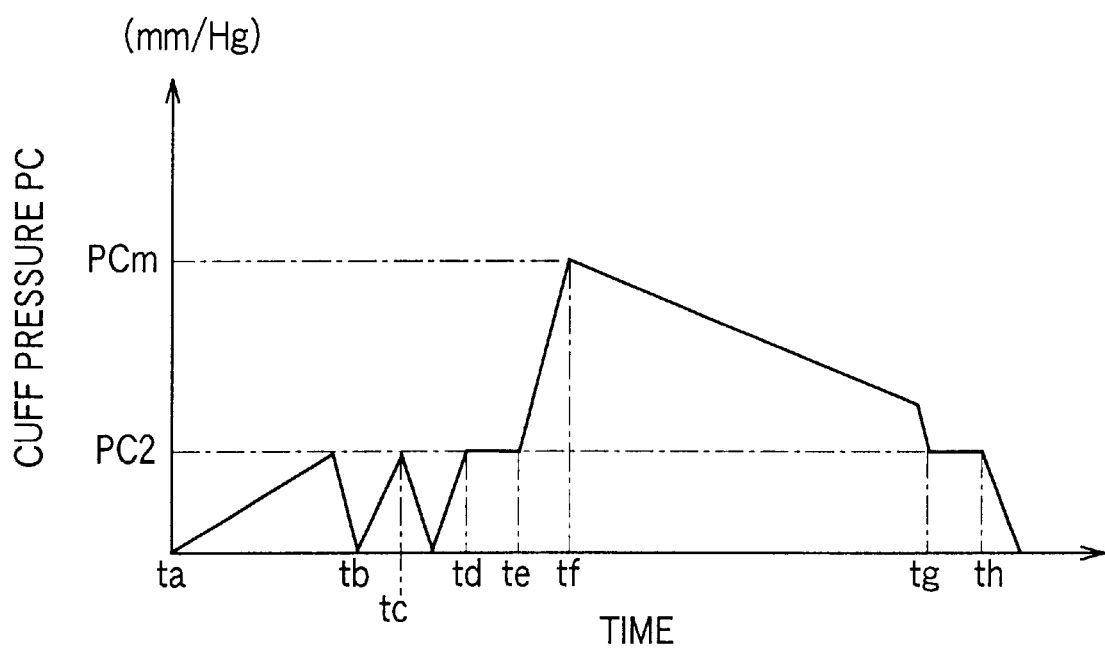
FIG. 12 is a time chart showing a time-wise change of a cuff pressure PC when the flow charts of FIGS. 10 and 11 are carried out.

In FIG. 10, when a measurement starting operation, not shown, is carried out, the control of the CPU starts with Step SC1 where the CPU actuates the air pump 24 and operates the pressure control valve 18 so as to start slow increasing of the cuff pressure PC at a rate of, e.g., 5 mmHg/sec, at a time, ta, shown in FIG. 12. While the cuff pressure PC is slowly increased, the CPU carries out SC2 through SC9 corresponding to the pulse-wave-detection-pressure determining portion 67.

Subsequently, at SC2, the CPU reads in, at a sampling period, a magnitude of the cuff-pulse-wave signal SM supplied from the pulse-wave filter circuit 28. SC2 is followed by SC3 to judge whether the CPU has read in a length of the signal SM that corresponds to one heartbeat of the subject. SC2 and SC3 are repeated till a positive judgment is made at SC3, while the CPU continues reading in the signal SM.

Meanwhile, if a positive judgment is made at SC3, the control goes to SC4 to normalize the heartbeat-synchronous pulse of the cuff pulse wave, read in by repeating Steps SC2 and SC3, such that the normalized pulse have prescribed amplitude and period.

Subsequently, at SC5, the CPU superposes the heartbeat-synchronous pulse of the cuff pulse wave, normalized at SC4 in the current control cycle, on the preceding heartbeat-synchronous pulse of the cuff pulse wave, normalized at SC4 in the preceding control cycle, and calculates a difference, d, by subtracting an area defined by the current pulse normalized at SC4 from an area defined by the preceding normalized pulse. However, since the initial heartbeat-synchronous pulse of the cuff pulse wave that is initially detected after the commencement of the slow increasing of the cuff pressure PC, has no preceding pulses, SC5 is not carried out for the initial pulse.

Then, at SC6, the CPU calculates a rate of change, r, of the difference d calculated at SC5 in the current control cycle, from the difference d calculated at SC5 in the preceding control cycle. However, since the first and second heartbeat-synchronous pulses of the cuff pulse wave that are initially detected after the commencement of the slow increasing of the cuff pressure PC, have no preceding difference values d, SC6 is not carried out for the first and second pulses.

Then, at SC7, the CPU judges whether the rate of change r calculated at SC6 is greater than a prescribed reference value, TH(r). In the case where no rate of change values r have been obtained, a negative judgment is made at SC7. If a negative judgment is made at SC7, the control repeats SC2 and the following steps.

Meanwhile, if a positive judgment is made at SC7, it means that deformation has occurred to the waveform of lower portion of heartbeat-synchronous pulse of the cuff pulse wave, and the control proceeds with SC8 to read in a current magnitude of the cuff-pressure signal SC supplied from the static-pressure filter circuit 26 and then with SC9 to determines, as a pulse-wave detection pressure PC2, a pressure lower by 20 mmHg than a cuff-pressure value PC represented by the cuff-pressure signal SC read in at SC8.

Subsequently, at SC10, the CPU stops the air pump 24, and operates the pressure control valve 18 so as to release the cuff pressure down to the atmospheric pressure, at a time, tb, shown in FIG. 12. In FIG. 10, SC1 and SC10 correspond to the low-speed pressure increasing portion 66a.

Then, the control goes to SC11 through SC13 corresponding to the preliminary pressing portion 66b. First, at SC11, the CPU starts again the air pump 24, and operates the pressure control valve 18 so as to start increasing of the cuff pressure PC. Then, at SC12, the CPU judges whether the cuff pressure PC has reached the pulse-wave detection pressure PC2 determined at SC9. SC12 is repeated till a positive judgment is made, while the increasing of the cuff pressure PC is continued. Meanwhile, a positive judgment is made at SC122, at a time, tc, shown in FIG. 12, and the control goes to SC13 to stop the air pump 24 and operate the pressure control valve 18 so as to release the cuff pressure PC down to the atmospheric pressure.

Subsequently, the control goes to SC14 and the following steps shown in FIG. 11. At SC14 corresponding to the first pulse-wave-detection-pressure keeping portion 66c, the CPU starts again the air pump 24 and operates the pressure control valve 18 so as to change and keep the cuff pressure PC to and at the pulse-wave detection pressure PC2 determined at SC9, at a time, td, shown in FIG. 12.

Then, at SC15, the CPU carries out the augmentation-index determining routine shown in FIG. 7, so as to read in not less than one heartbeat-synchronous pulse of the cuff pulse wave, determine an augmentation index AI based on the thus read-in pulse, and operate the display device 42 to display the thus determined augmentation index AI.

Subsequently, at SC16, the CPU determines, based on the cuff pulse wave read in by carrying out the augmentation-index determining routine at SC15, a heart rate HR in the same manner as that employed at SA7 of FIG. 5, and operates the display device 42 to display the thus determined heart rate HR.

Then, at SC17, the CPU operates, for a blood-pressure measurement, the pressure control valve 18 so as to start quick increasing of the cuff pressure PC, at a time, te, shown in FIG. 12. SC17 is followed by SC18 to judge whether the cuff pressure PC has exceeded the prescribed target pressure value Pcm, e.g., 180 mmHg. SC18 is repeated until a positive judgment is made, while the cuff pressure PC is quickly increased. Meanwhile, if at a time, tf, shown in FIG. 12 the cuff pressure PC has exceeded the target pressure PCm and accordingly a positive judgment is made at SC18, the control goes to S19 to stop the air pump 24 and operate the pressure control valve 18 to slowly decrease the cuff pressure PC at a low rate of from 3 to 5 mmHg/sec.

Then, at SC20, the CPU reads in a one-heartbeat length of the cuff-pressure signal SC supplied from the static-pressure filter circuit 26 and a one-heartbeat length of the cuff-pulse-wave signal SM supplied from the pulse-wave filter circuit 28. Subsequently, the control goes to S21 corresponding to the blood-pressure determining portion 68. At S21, the CPU determines, based on change of respective amplitudes of a plurality of heartbeat-synchronous pulses of the cuff pulse wave continuously obtained at S20 during the slow decreasing of the cuff pressure PC, a systolic blood pressure $BP_{SYS}$, a mean blood pressure $BP_{MEAN}$, and a diastolic blood pressure $BP_{DIA}$ of the subject, according to well-known oscillometric method. Then, at SC22, the CPU judges whether all blood-pressure values BP have been determined at SC21. S20 through S22 are repeated until a positive judgment is made at S22, while the current blood-pressure measuring operation is continued. Meanwhile, if a positive judgment is made at S22, the control goes to S23 to operate the display device 42 to display the thus determined systolic blood pressure $BP_{SYS}$, mean blood pressure $BP_{MEAN}$, and diastolic blood pressure $BP_{DIA}$ of the subject, determined at SC21. Here, if a positive judgment is made at SC22, the CPU carries out SC23 and the following steps and changes and keeps, at SC24, described later, the cuff pressure PC to and at the pulse-wave detection pressure PC2, thereby ending the slow decreasing of the cuff pressure PC. Thus, if a positive judgment is made at SC22, the slow decreasing of the cuff pressure PC is ended. Therefore, SC17 through SC19 and SC22 correspond to the blood-pressure-measurement-related pressure changing portion 66d.

After the blood-pressure values BP are displayed at SC23, the CPU carries out SC24 through SC26 that are identical with SC14 through SC16. More specifically described, at SC24 corresponding to the second pulse-wave-detection-pressure keeping portion 66e, the CPU again changes and keeps the cuff pressure PC to and at the pulse-wave detection pressure PC2, at a time, tg, shown in FIG. 12. Then, at SC25, the CPU carries out the augmentation-index determining routine shown in FIG. 7, so as to determine an augmentation index AI and operate the display device 42 to display the thus determined augmentation index AI. Subsequently, at SC26, the CPU determines a heart rate HR and operates the display device 42 to display the thus determined heart rate HR. In FIG. 11, SC15 and SC25 correspond to the augmentation-index determining portion 70, and SC16 and SC26 correspond to the heart-rate determining portion 72.

Then, at SC27, the CPU operates the pressure control valve 18 to release the cuff pressure PC down to the atmospheric pressure, at a time, th, shown in FIG. 12.

It emerges from the foregoing description of the second embodiment that, before the blood-pressure-measurement-related pressure changing portion 66d (SC17 through SC19 and SC22) carries out the blood-pressure-measurement-related pressure changing operation to press the upper arm 14, and after the changing portion 66d carries out the changing operation to completely stop the flow of blood in the upper arm 14 and subsequently sufficiently decrease the cuff pressure PC, the augmentation-index determining portion 70 (SC15 and SC25) determines respective augmentation-index values AI of the subject. Therefore, the medical person can evaluate the function of vascular endothelial cells of the subject, based on a degree of change of the augmentation index AI determined after the blood-pressure-measurement-related pressure changing operation, from the index AI determined before the same. Since it is not needed to employ an ultrasound diagnostic device, it is easy to evaluate the function of vascular endothelial cells.

Also, in the present embodiment, the preliminary pressing portion 66b (SC11 through SC13) carries out the preliminary pressing of the upper arm 14, the cuff 12 and the body portion 14 on which the cuff 12 is worn are brought into close contact with each other. Therefore, a more accurate cuff pulse wave can be detected and accordingly a more accurate augmentation index AI can be determined based on the cuff pulse wave. Thus, the medical person can more accurately evaluate the function of vascular endothelial cells of the subject.

Also, in the present embodiment, the pulse-wave-detection-pressure determining portion 67 (SC2 through SC9) determines the pulse-wave detection pressure PC2 based on the cuff pulse wave actually detected during the slow increasing of the cuff pressure PC. Thus, in each measuring operation, the most appropriate pulse-wave detection pressure PC2 is determined. Therefore, the respective cuff pulse waves detected in the state in which the cuff pressure PC is kept at the pulse-wave detection pressure PC2 by the first pulse-wave-detection-pressure keeping portion 66c and in the state in which the cuff pressure PC is kept at the detection pressure PC2 by the second keeping portion 66e, have an accurate waveform, and accordingly the augmentation-index determining portion 70 (SC15 through SC25) determines an accurate augmentation index AI based on each of the accurate cuff pulse waves. Thus, the medical person can more accurately evaluate the function of vascular endothelial cells of the subject based on the accurate augmentation-index values AI.

Also, in the present embodiment, the augmentation-index determining portion 70 (SC15 and SC25) time-wise determines the augmentation-index values AI based on the cuff pulse waves extracted by the pulse-wave filter circuit 28 in the state in which the cuff pressure PC is controlled by the cuff-pressure changing portion 66 (SC14, SC17 through SC19, SC22, SC24), and additionally the blood-pressure determining portion 68 (SC21) determines the blood-pressure values BP. Thus, the present apparatus simultaneously allows the evaluation of the function of the vascular endothelial cells and the determination of the blood-pressure values BP.

Also, in the present embodiment, the heart-rate determining portion 72 (SC16 and SC26) determines a heart rate HR of the subject, before the blood-pressure-measurement-related pressure changing portion 66d (SC17 through SC19 and SC22) carries out the blood-pressure-measurement-related pressure changing operation to press the upper arm 14, and after the changing portion 66d carries out the changing operation to completely stop the flow of blood in the upper arm 14 and subsequently sufficiently decrease the cuff pressure PC. Thus, the medical person can judge, based on a degree of change of the heart rate HR determined after the changing operation from the heart rate HR determined before the same, whether the activity of the autonomic nerve of the subject is normal. Thus, the present apparatus simultaneously allows not only the evaluation of the function of the vascular endothelial cells and the determination of the blood-pressure values BP, but also the evaluation of the activity of the autonomic nerve.

While the present invention has been described in its preferred embodiments by reference to the drawings, it is to be understood that the invention may otherwise be embodied.

For example, in each of the illustrated embodiments, the augmentation index AI is obtained as the pulse-wave second-half information. However, it is possible to obtain, as the pulse-wave second-half information, a degree of sharpness of heartbeat-synchronous pulse of pulse wave; a diastolic area of heartbeat-synchronous pulse of pulse wave; a time constant of a portion of heartbeat-synchronous pulse of pulse wave that is subsequent to the peak or diastolic early plateau thereof; or the greatest slope of a portion of heartbeat-synchronous pulse of pulse wave that is subsequent to the diastolic early plateau thereof.

Figure 13:
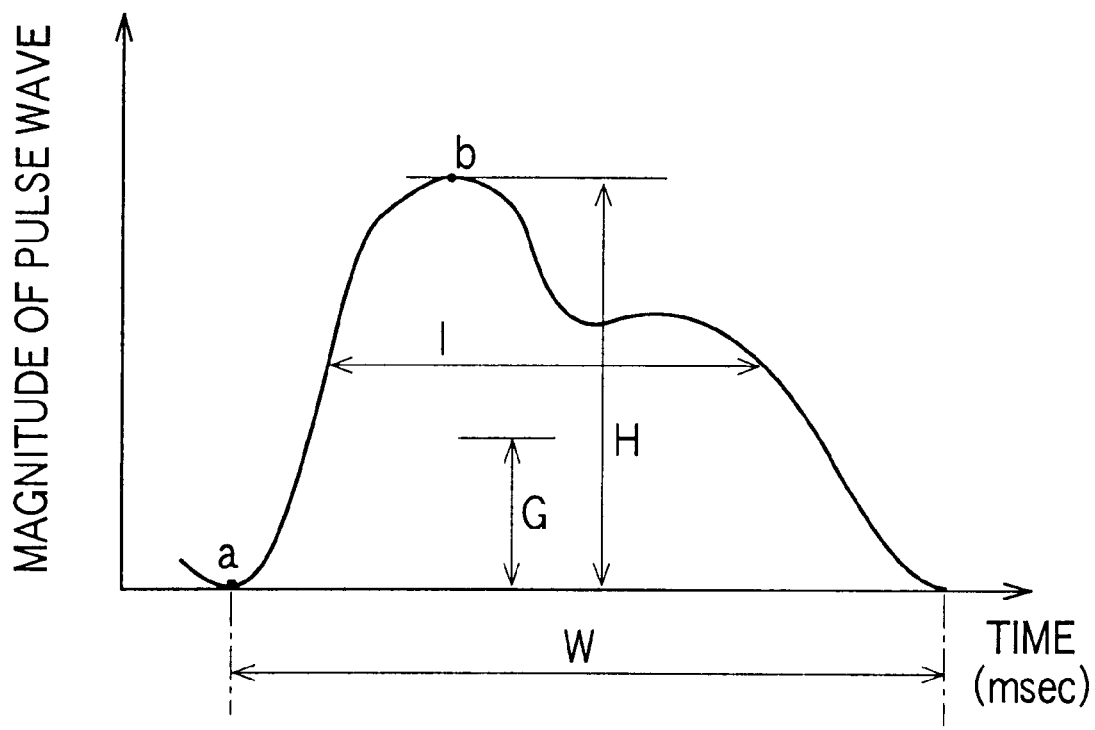
FIG. 13 is a view for explaining a degree of sharpness of a pulse wave.

The degree of sharpness may be any one of a normalized pulse-wave area, VR, that is calculated by dividing a pulse-wave area, S, obtained by integrating (summing) a one-heartbeat length of pulse wave, shown in FIG. 13, by the product (W×H) of a peak height, H, and a pulse-wave period, W, i.e., according to the following expression: VR=S/(W×H); a value obtained by normalizing an area S1 defined by a second-half portion subsequent to peak, b; or a value, I/W, obtained by normalizing a width, I, at a height equal to H×(2/3). The normalized pulse-wave area VR may be called % MAP, and may be calculated as a proportion (=100×G/H) of a height, G, of a gravity center of the pulse-wave area S to the peak height H, i.e., pulse pressure. Since a heartbeat-synchronous pulse of pulse wave can be divided by a notch into a systolic portion and a diastolic portion, the diastolic area of pulse wave is defined as an area defined by a portion of the pulse that is subsequent to the notch; and the diastolic early plateau is defined as the first local maximum point subsequent to the notch.

Also, in each of the illustrated embodiments, the cuff 12 is worn the upper arm 14. However, the cuff 12 may be worn on a different body portion of the subject, such as a femoral portion or an ankle.

Also, in each of the illustrated embodiments, the cuff 12, the pressure sensor 16, and the pulse-wave filter circuit 28 cooperate with each other to provide the pulse-wave detecting device that detects the pulse wave from the body portion on which the cuff 12 is worn. However, it is possible to wear a pulse-wave detecting device on a distal portion, e.g., a wrist, of the subject with respect to the cuff 12. In the case where the pulse-wave detecting device worn on the distal side of the body portion on which the cuff is worn, is used to detect a pulse wave, it is not needed to keep the cuff pressure PC at the pulse-wave detection pressure PC2, unlike in each illustrated embodiment. For example, the cuff pressure PC at which the pulse-wave detecting device detects a pulse wave used to obtain pulse-wave second-half information, may be equal to atmospheric pressure.

Also, in each of the illustrated embodiments, before or after the cuff pressure PC is increased up to the pressure that stops the flow of blood in the cuff-pressed portion of the subject, the cuff pressure PC is kept at the pulse-wave detection pressure PC2 lower than the diastolic blood pressure $PB_{DIA}$ of the subject and, in this state, a cuff pulse wave is detected to be used to determine an augmentation index. However, it is possible to obtain pulse-wave second-half information based on a pulse wave that is detected in a state in which the cuff pressure PC is kept at a pressure higher than the mean or systolic blood pressure $BP_{MEAN}$, $BP_{SYS}$ of the subject.

Also, in the foregoing description, the cuff pulse wave used to determine the augmentation index AI is obtained in the state in which the cuff pressure PC is kept at the pre-determined pulse-wave detection pressure PC2. However, it is possible to detect a cuff pulse wave to be used to determine an augmentation index AI, while the cuff pressure PC is changed.

Also, in the illustrated first embodiment, the augmentation index values AI are iteratively determined after the cuff pressure PC is decreased to the pulse-wave detection pressure PC2. However, a time-wise change of augmentation index AI can be observed based on two augmentation index values AI determined at two different times. Thus, according to the present invention, it is required that at least two augmentation index values AI be determined at at least two different times. In addition, if at least one of the two augmentation index values is determined at at least one time in the waveform deformation period, a change of augmentation index AI, caused by the pressing of the pressing device, can be observed, even if the other augmentation index AI may be determined outside the above-indicated period. Therefore, according to the present invention, it is required that at least one of at least two augmentation index values be determined at a time in the waveform deformation period.

Also, in the illustrated second embodiment, it is possible to calculate a difference between the respective augmentation index values AI measured before and after the blood-pressure measurement, and a ratio of one of the two augmentation index values AI to the other, and operate the display device 42 to display the thus calculated difference or ratio. In this case, a degree of change of the augmentation index values AI can be easily recognized.

Also, in the illustrated second embodiment, the blood-pressure-measurement-related pressure changing portion 66d carries out the one-time blood-pressure-measurement-related pressure changing operation. However, the changing portion 66d may be modified to carry out two or more pressure changing operations.

In addition, generally, augmentation index AI is calculated according to the mathematical expression (Expression 1) wherein the denominator is pulse pressure PP. However, even in the case where the denominator is replaced with an amplitude of cuff pulse wave at the time of occurrence of peak point of the incident-wave component or at the time of occurrence of peak point of the reflected-wave component, a value calculated according to the thus modified expression reflects a condition of vascular endothelial cells of the subject. Therefore, in Expression 1, pulse pressure PP may be replaced with amplitude of cuff pulse wave at the time of occurrence of peak point of the incident-wave component or at the time of occurrence of peak point of the reflected-wave component.

In each of the illustrated embodiments, the heart rate HR is obtained as the heart-rate-related information. However, it is possible to obtain a pulse period, RR, as the heart-rate-related information.

It is to be understood that the present invention may be embodied with other changes, improvements, and modifications that may occur to a person skilled in the art without departing from the spirit and scope of the invention.

What is claimed is:

1. A vascular-endothelial-cell-function evaluating apparatus comprising:
   a pressing device including a cuff that is adapted to be worn on a first portion of a living subject, and a cuff-pressure changing device that changes a pressure in the cuff so as to press the first portion of the subject in a pressing period;
   a pulse-wave detecting device that detects a pulse wave including a plurality of heartbeat-synchronous pulses, from the first portion of the subject, or a second portion of the subject located on a distal side of the first portion; and
   a pulse-wave-second-half-information obtaining device that obtains a plurality of sets of pulse-wave-second-half information that represent respective characteristics of respective second-half portions of respective heartbeat-synchronous pulses of the pulse wave that are detected by the pulse-wave detecting device at respective different times, the respective second-half portions of the respective heartbeat-synchronous pulses being respective portions of the respective pulses that are subsequent to respective peak points of the respective pulses, the pulse-wave-second-half-information obtaining device providing a time-wise change of the sets of pulse-wave-second-half information that is caused by the pressing of the pressing device.

2. A vascular-endothelial-cell-function evaluating apparatus according to claim 1, wherein the pressing device presses, with the cuff, the first portion of the subject so as to stop a flow of blood in the first portion, and subsequently decreases the pressure of the cuff down to a pressure not higher than a mean blood pressure of the first portion, and
   wherein the pulse-wave-second-half-information obtaining device obtains the sets of pulse-wave-second-half information in a waveform-deformation period in which the pressure of the cuff has already been decreased to the pressure not higher than the mean blood pressure of the first portion and respective waveforms of the respective heartbeat-synchronous pulses of the pulse wave are deformed yet as a result of the pressing of the pressing device.

3. A vascular-endothelial-cell-function evaluating apparatus according to claim 1, wherein the cuff-pressure changing device of the pressing device includes a blood-flow stopping device for increasing the pressure of the cuff up to a pressure higher than a systolic blood pressure of the first portion of the subject, so as to stop a flow of blood in the first portion; a first pulse-wave-detection-pressure keeping device for keeping, before the blood-flow stopping device increases the pressure of the cuff, the pressure of the cuff at a pulse-wave detection pressure not higher than a mean blood pressure of the first portion, for a time duration corresponding to at least one heartbeat of the subject; and a second pulse-wave-detection-pressure keeping device for keeping, after the blood-flow stopping device increases the pressure of the cuff, the pressure of the cuff at a pulse-wave detection pressure not higher than a mean blood pressure of the first portion, for a time duration corresponding to at least one heartbeat of the subject,
   wherein the pulse-wave detecting device detects a cuff pulse wave that is transmitted from the first portion of the subject to the cuff, and
   wherein the pulse-wave-second-half-information obtaining device obtains one of the sets of pulse-wave-second-half information from a cuff pulse wave detected by the pulse-wave detecting device in a state in which the pressure of the cuff is kept at the pulse-wave detection pressure by the first pulse-wave-detection-pressure keeping device, and obtains the other set of pulse-wave-second-half information from a cuff pulse wave detected by the pulse-wave detecting device in a state in which the pressure of the cuff is kept at the pulse-wave detection pressure by the second pulse-wave-detection-pressure keeping device.

4. A vascular-endothelial-cell-function evaluating apparatus according to claim 3, wherein the cuff-pressure changing device of the pressing device further includes a pressure increasing device for increasing, before the first pulse-wave-detection-pressure keeping device keeps the pressure of the cuff at the pulse-wave detection pressure, the pressure of the cuff from a pressure lower than a diastolic blood pressure of the first portion of the subject, and wherein the apparatus further comprises a pulse-wave-detection-pressure determining device for determining the pulse-wave detection pressure based on a fact that a deformation occurs to a waveform of a heartbeat-synchronous pulse of the cuff pulse wave continuously detected by the pulse-wave detecting device while the pressure of the cuff is increased by the pressure increasing device.

5. A vascular-endothelial-cell-function evaluating apparatus according to claim 3, wherein the cuff-pressure changing device of the pressing device further includes a preliminary pressing device for increasing, before the first pulse-wave-detection-pressure keeping device keeps the pressure of the cuff at the pulse-wave detection pressure, the pressure of the cuff up to the pulse-wave detection pressure, by a predetermined number of times, so as to preliminarily press the first portion of the subject.

6. A vascular-endothelial-cell-function evaluating apparatus according to claim 5, wherein the cuff-pressure changing device of the pressing device further includes a pressure increasing device for increasing, before the preliminary pressing device increases the pressure of the cuff, the pressure of the cuff from a pressure lower than a diastolic blood pressure of the first portion of the subject, and wherein the apparatus further comprises a pulse-wave-detection-pressure determining device for determining the pulse-wave detection pressure based on a fact that a deformation occurs to a waveform of a heartbeat-synchronous pulse of the cuff pulse wave continuously detected by the pulse-wave detecting device while the pressure of the cuff is increased by the pressure increasing device.

7. A vascular-endothelial-cell-function evaluating apparatus according to claim 3, wherein the blood-flow stopping device comprises a blood-pressure-measurement-related pressure changing device for increasing the pressure of the cuff up to the pressure higher than the systolic blood pressure of the first portion of the subject, and subsequently decreasing the pressure of the cuff, and wherein the apparatus further comprises a blood-pressure determining device for determining a blood pressure of the subject based on a cuff pulse wave detected by the pulse-wave detecting device while the pressure of the cuff is decreased by the blood-pressure-measurement-related pressure changing device.

8. A vascular-endothelial-cell-function evaluating apparatus according to claim 1, wherein each of the sets of pulse-wave-second-half information comprises an augmentation index indicating a proportion of a reflected-wave component of the pulse wave to an incident-wave component thereof.

9. A vascular-endothelial-cell-function evaluating apparatus according to claim 1, wherein each of the sets of pulse-wave-second-half information comprises a degree of sharpness of the pulse wave.

10. A vascular-endothelial-cell-function evaluating apparatus according to claim 1, wherein each of the sets of pulse-wave-second-half information comprises a diastolic area of the pulse wave.

11. A vascular-endothelial-cell-function evaluating apparatus according to claim 1, further comprising a heart-rate-related-information obtaining device that obtains a plurality of sets of heart-rate-related information each of which is related to a heart rate of the subject, based on respective heartbeat-synchronous pulses of the pulse wave that are detected by the pulse-wave detecting device at respective different times, the heart-rate-related-information obtaining device providing a time-wise change of the sets of heart-rate-related information that is caused by the pressing of the pressing device.

12. A vascular-endothelial-cell-function evaluating apparatus according to claim 1, wherein the pulse-wave-second-half-information obtaining device comprises a display device that displays the plurality of sets of pulse-wave-second-half information, and thereby provides the time-wise change of the sets of pulse-wave-second-half information that is caused by the pressing of the pressing device.

* * * * *